(12) United States Patent
Pryor et al.

(10) Patent No.: US 6,329,572 B1
(45) Date of Patent: *Dec. 11, 2001

(54) PLANT PROMOTER ACTIVATED BY FUNGAL INFECTION

(75) Inventors: Anthony J. Pryor, Canberra (AU); James K. Roberts, St. Louis, MO (US)

(73) Assignee: Commonwealth Scientific and Industrial Research Organisation, Campbell (AU)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/952,061

(22) PCT Filed: May 3, 1996

(86) PCT No.: PCT/AU96/00264

§ 371 Date: Feb. 18, 1998

§ 102(e) Date: Feb. 18, 1998

(87) PCT Pub. No.: WO96/34949

PCT Pub. Date: Nov. 7, 1996

(30) Foreign Application Priority Data

May 5, 1995 (AU) .................................................. PN2834

(51) Int. Cl.⁷ ............................. A01H 5/00; C12N 15/82; C07H 21/04
(52) U.S. Cl. ..................... 800/298; 435/320.1; 536/24.1; 800/278
(58) Field of Search ........................ 536/24.1; 435/320.1, 435/419, 468; 800/279, 301, 278, 298

(56) References Cited

FOREIGN PATENT DOCUMENTS

| | | |
|---|---|---|
| WO91/15585 | 10/1991 | (WO) . |
| WO 93/19188 * | 9/1993 | (WO) . |
| WO95/03690 | 2/1995 | (WO) . |
| WO95/33818 | 12/1995 | (WO) . |

OTHER PUBLICATIONS

Stam M, et al. "The silence of genes in transgenic plants." Ann. Bot. 79: 3–12, 1997.*
Koziel MG, et al. "Optimizing expression of transgenes with an emphasis on post–transcriptional events." Plant Mol. Biol. 32: 393–405, 1996.*
Smith CJS, et al. "Antisense RNA inhibition of polygalacturonase gene expression in transgenic tomatoes." Nature 334: 724–726, Aug. 25, 1988.*
Benfey PN, et al. "The cauliflower mosaic virus 35S promoter: Combinatorial regulation of transcription in plants." Science 250: 959–966, Nov. 1990.*
Kim Y, et al. "A 20 nucleotide element is essential for the nopaline synthase (nos) promoter activity." Plant Mol. Biol. 24: 105–117, 1994.*
J. Cell. Biochem. 19B: 153. Keystone Symposium on Host–Fungus Pathogenic Interactions, Feb. 26, 1995.*
Castresana et al., Tissue–Specific and Pathogen–Induced Regulation of a *Nicotiana plumbaginifolia* β–1,3–Glucanase Gene, Plant Cell, vol. 2, No. 12, pp. 1131–1143, Dec. 1990, XP–002146377.
Gough et al., "Developmental and pathogen–induced activation of an msr gene, str. 246C, from tobacco involves multiple regulatory elements", Molecular and General Genetics (1995) 247 (3)323–327, XP–002146378.
Samac et al., "Developmental and Pathogen–Induced Activation of the Arabidopsis Acidic Chitinase Promoter", Plant Cell, vol. 3, No. 10, 1063–1072, Oct. 1991, XP–002146376.
Roberts et al., Isolation of a flax (*Linum usitatissimum*) gene induced during susceptible infection by flax rust (*Melampsora lini*), Plant Journal (Jul. 1995), 8(1), pp. 1–8, XP–00091841.
Developmental and tissue–specific expression of a tomato anionic peroxidase (tapl) gene by a minimal promoter, with wound and pathogen induction by an additional 5'–flanking region, Royce Mohan, et al., Plant Molecular Biology 22:475–490, 1993.
Inhibition of Fungal Disease Development in Plants by Engineering Controlled Cell Death, Gunter Strittmatter, et al. Biotechnology vo. 13, Oct. 1995, pp. 1085–0189.
5' Upstream Sequences from the wun1 Gene are Responsible for Gene Activation by Wounding in Transgenic Plants, Jurgen Logemann, et al., The Plant Cell, vol. 1, 151–158, Jan. 1989 American Society of Plant Physiologists.

* cited by examiner

Primary Examiner—Amy J. Nelson
(74) Attorney, Agent, or Firm—Bacon & Thomas

(57) ABSTRACT

The present invention relates generally to genetic sequences which confer, activate, or enhance expression of a gene in a plant, in response to infection of said plant by a plant fungal pathogen in a susceptible interaction. The invention further provides genetic sequences such as structural genes, the expression of which is induced in response to a susceptible interaction between a plant and a fungal pathogen.

17 Claims, 8 Drawing Sheets

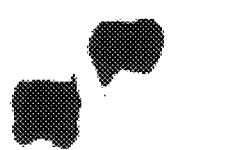
← 23.1kb
← 9.42kb
← 6.56kb
← 4.37kb
← 2.3kb
← 2.07kb
← 0.56kb
FIG. 1

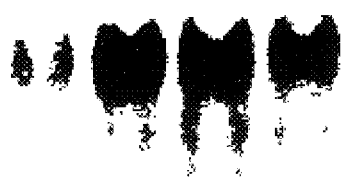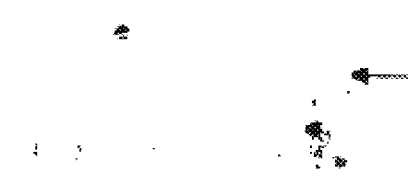
FIG. 3

1 2 3 4 5 6 7
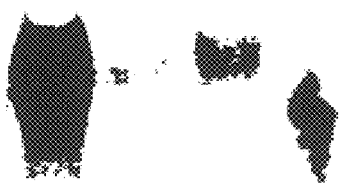
a
b
c
FIG. 4

FIG. 5

```
                GPL motif
mls: NFPLEIPLLQLMGALYMGNKPVLKVDSKVSIVMEQMIRLLHDCGLPAEDMDFINSDGAVM
     NFPLEIP+LQLMGALYMGNKP+LKVDSKVSIVMEQM+RLLH CGLP  D DF+NSDG  M
fls: NFPLEIPVLQLMGALYMGNKPLLKVDSKVSIVMEQMMRLLHYCGLPVGDADFVNSDGKAM
     203                                                      262

GSG motif
mls:NKLLLEANPKMTLFTGSSRVAEKLAADLKGRVKLEDAGFDWKILGPDV
    NK+LLEANP+MTLFTGSSRVAEKLA DLKGR+KLEDAGFDWKILGPDV
fls:NKILLEANPRMTLFTGSSRVAEKLALDLKGRIKLEDAGFDWKILGPDV
    263                                          310 active site
mls:DYVAWVCDQDAYACSGQKCSAQSVLFMHK
    DYVAWVCDQDAYACSGQKCSAQS+LFMH+
fls:DYVAWVCDQDAYACSGQKCSAQSILFMHE
    314                        342

EEP motif
mls:LTVTTEAMLEHMNNLLKIRGSKVLFGGEPLANHSIPKIYGAMKPTAVFVPLEEILKSGNFELVTKEIFGP
    LTVTTEAML+H+N LL+I G+K+LFGG+PL NH+IP IYGA+KPTAV+VPLEEILK  N+ELVTKEIFGP
fls:LTVTTEAMLDHLNKLLQIPGAKLLFGGKPLENHTIPSIYGAVKPTAVYVPLEEILKVSNYELVTKEIFGP
    371                                                              440
```

PLANT PROMOTER ACTIVATED BY FUNGAL INFECTION

CROSS-REFERENCES TO RELATED APPLICATIONS

This application is the U.S. national phase of PCT/AU96/00264 filed on May 3, 1996.

BACKGROUND OF THE INVENTION

1. Field of the Invention

The present invention relates generally to genetic sequences which are useful in the diagnosis and treatment of fungal infections in plants which involve a susceptible interaction between a fungal pathogen and the host plant In particular, the present invention provides genetic sequences which confer, activate, or enhance expression of a gene in a plant, in response to infection of said plant by a plant fungal pathogen in a susceptible interation. The invention further provides genetic sequences such as structural genes, the expression of which is induced in response to a susceptible interaction between a plant and a fungal pathogen. The present invention further provides methods for the detection of infection by a fungal pathogen in a susceptible interaction and for the production of transgenic plants with improved resistance to said fungal pathogen. The present invention is particularly useful for developing disease resistance in crop varieties.

2. Background of the Information

Advances in plant biotechnology have dramatically altered the approaches taken to increase the economic output of productive units of agriculture. Of major significance to the agricultural and horticultural industries are the reduced productivity, due to infection by plant pathogens. Plant fungal pathogens, in particular rust fungi, represent an especially significant problem amongst broadacre crops such as legume and cereal grains. Biotechnology offers considerable scope for addressing this problem, by introducing recombinant genes into plant that either kill or disable a fungal pathogen, or restrict a fungal pathogen to a limited zone of infection, thereby preventing significant deterioration of an economically-important crop. Thus, the development of disease resistant plants by biotechnological means, is an important goal in agricultural and horticultural research.

Genetic analyses indicate that rust resistance genes of the plant genome control specific recognition of the products of rust avirulence genes. An interaction between a rust pathogen and a plant host may be classed as either "resistant" or "susceptible" depending on how the fungal infection proceeds. In a resistant interaction, infection by a fungal pathogen produces a "plant hypersensitive response" (Marineau et al., 1987; Dixon and Lamb, 1990) resulting in cell death to limit spread of the fungus. During the hypersensitive response, the expression of several infection-related genes, for example genes encoding phytoalexins, antimicrobial agents and pathogenesis-related (PR) proteins, is switched on. In contrast, a susceptible interaction involves no hypersensitive cell death and the infection alters host cell gene expression in such a way as to provide gene products that are essential for the biotrophic growth of an obligate plant pathogen. Thus, the two processes are quite distinct, involving different host cell genes and mechanisms regulating the expression of said host cell genes. This distinction is of paramount importance. For example, those host genes induced in a susceptible interaction may be essential to allow the rust to grow in the plant tissues.

Most studies have concentrated on identifying and manipulating genes encoding proteins involved in the hypersensitive response of the resistant interaction (Collinge and Slusarenko, 1987; Dixon and Lamb, 1990; Keen, 1992; van Loon, 1985; Ohashi and Ohshima, 1992). Marlini and Strittmatter (Patent Application WO 9319188) have constructed a fungus-responsive chimaeric gene, using a promoter sequence from the prp1 gene, in particular the prp1-1 gene, to direct expression of a "killer" gene in plant cells infected by a fungal pathogen. However the prp1 genetic sequence is induced in a resistant interaction only (i.e. in a pathogenesis-related fungal infection). Although genetic sequences such as the prp1 gene may provide a means of control of a pathogen in a resistant interaction, the isolation of host cell genetic sequences involved in a susceptible interaction between a plant and a fungal pathogen has not been a straightforward procedure.

In full-susceptible interactions between the flax plant *Linum usitatissimum* and the flax rust *Melampsora lini*, there is no immediate host cell death or chlorosis. Instead, host cell metabolism is directed toward the production of viable fungal spores, including for example, the translocation of photosynthates via the haustorium or lungal absorptive organ to the fungal mycelium. Although altered patterns of protein synthesis have been observed following a susceptible rust infection of flax plants (Sutton and Shaw, 1986), it has not been possible, until the present invention, to differentiate between fungal protein synthesis and modifications to plant protein synthesis. Thus, the isolation of flax genetic sequences, the expression of which is induced during a susceptible rust infection, has not been a straightforward procedure.

Bibliographic details of the publications referred to by author in this specification including information disclosed under 37 C.F.R. §1.97 and 1.98, are collected at the end of the detailed description of the invention.

SUMMARY OF THE INVENTION

In work leading up to the present invention, the inventors sought to develop plants with improved resistance to fungal pathogens which would otherwise infect the plant in a susceptible interaction. Accordingly, the inventors identified plant genetic sequences in flax and maize, the expression of which increases in response to a susceptible rust infection. The cloning of these sequences provides a means of generating transgenic plants with de novo, improved, or otherwise enhanced antifungal properties. In particular, by placing a cytotoxic gene, anti-fungal gene, antisense, ribozyme or co-supression molecule operably under control of a promoter sequence derived from a genetic sequence which is normally tanscriptionally up-regulated in response to a susceptible infection, and introducing the resulting chimeric gene into a plant, disease resistance against said fungal pathogen is conferred or otherwise facilitated in said plant The present invention also permits the screening, through genetic or immunological means, similar susceptible reaction-responsive (SRR) genetic sequences in other plants, for use in developing or enhancing the antigal properties of commercially- and economically-important species.

BRIEF DESCRIPTION OF THE DRAWINGS

FIG. 1 is a photographic representation of a Southern blot hybridisation demonstrating the origin of pFIS1 from the flax genome. Equal amounts (10 µg) of flax DNA (lanes 1 to 3) and rust DNA (lanes 4 to 6) were digested with the restriction enzymes, BglII (lanes 1 and 4), EcoRI (lanes 2 and 5) and HindIII (lines 3 and 6). The DNA was transferred to membrane and probed with pFIS 1.

Figure 2A:
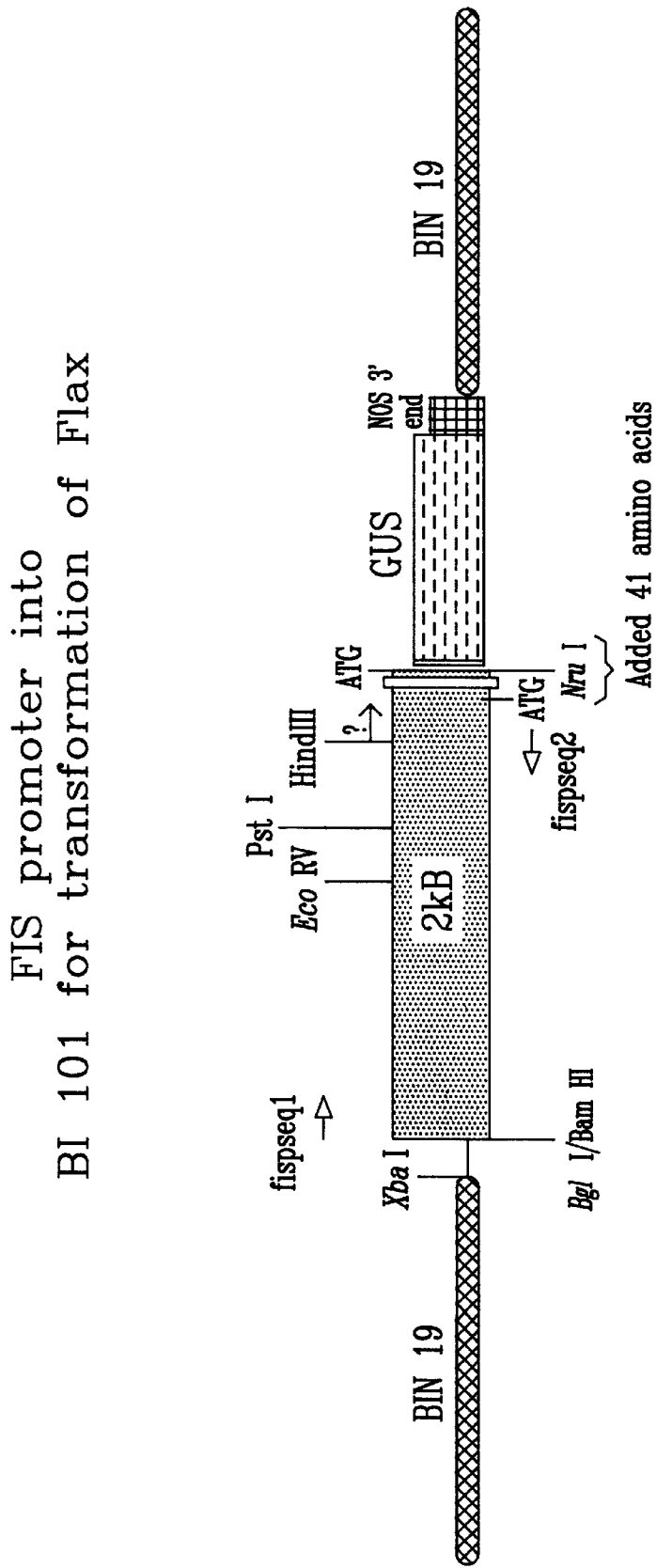

FIG. 2A is a schematic representation of a recombinant DNA molecule comprising the bacterial β-glucuronidase (uidA) structural gene placed operably under control of the flax Fis1 gene promoter sequence. The hatched area indicates the Fis1 promoter. The filled-in area indicates the β-glucuronidase structural gene.

Figure 2B:

FIG. 2B is a photographic representation showing GUS reporter gene expression under control of the flax Fis1 gene promoter sequence, in leaf cells of a transgenic flax plant carrying the recombinant DNA molecule of FIG. 2(a), following infection with *Melampsora lini*. GUS gene expression which appears as intense blue colouration in plant cells, following staining with X-glucuronide, is indicated in the Figure by the dark spotted regions. Original colour prints are available from the applicant upon request.

FIGS. 3A–3C is a photographical representations of Northern blots showing the level of Fis1 mRNA during susceptible rust infection. Each lane contains 20 μg of total RNA isolated from germinated rust spores (1), leaves from susceptible flax plant 1 day after inoculation with rust spores (2), 2 days after inoculation (3), leaves 3 days after inoculation (4), 4 days after inoculation (5), 5 days after inoculation (6), 6 days after inoculation (7) and uninfected leaves (8). The arrows indicate the position of the large and small ribosomal RNAs.

A) The filter was hybridised with the coding region of the Fis1 structural gene.

B) To demonstrate that approximately equal amounts of RNA were loaded the same filter as in A was hybridised with a flax cDNA, pFCS1 (Flax Constant Sequence) that does not change during infection (note that exposure was 5 times longer than when probed with pFIS1).

C) The same filter hybridised with an anionic peroxidase cDNA cloned (see Materials and Methods for complete description of peroxidase clone).

FIGS. 4A–4C are photographic representations of Northern blots showing the level of Fis1 mRNA during resistant infections of flax with flax rust. Each lane contains 20 μg per lane of total RNA from leaves of a susceptible plant 5 days after inoculation (1) and RNA from leaves of resistant flax, uninfected (2) 1 day after inoculation (3), 2 days (4), 3 days (5) and 4 days (6), and 5 days (7) after inoculation.

A) The filter was hybridised with pFIS1.

B) The same filter hybridised with an anionic peroxidase cDNA demonstrating the induction of this PR protein during the resistant infection.

C) The same filter as in A probed with flax cDNA pFCS1 as a control to demonstrate equal loading of each lane.

FIG. 5 is a graphical representation showing a comparison of the amino acid sequences of the maize Mis1 (row 1) and flax Fis1 (row 3) SR gene product motifs, including the GPL motif, GSG motif, EEP motif and active site incorporating the GQG motif. Row 2 in each case shows conserved amino acid residues, with conservative amino acid substitutions indicated by the plus sign (+).

Figure 6:
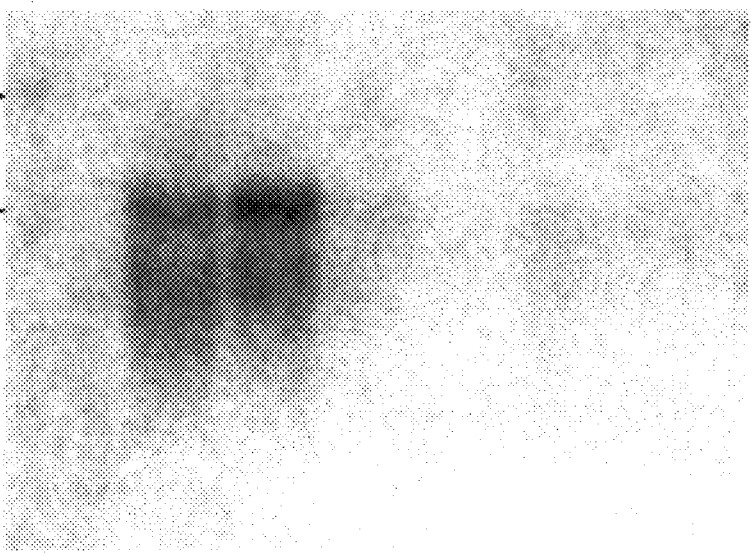

FIG. 6 is a photographic representation of a northern blot showing the induction of mRNA during the five day period following infection of susceptible maize plants with *Puccinia sorghi* race 1. Each lane contains approximately 30 μg of total RNA isolated from leaves of uninfected plants (lane 1) or infected plants, harvested 2, 3, 4 or 5 days post-infection (lanes 2 to 5 respectively).

Figure 7:
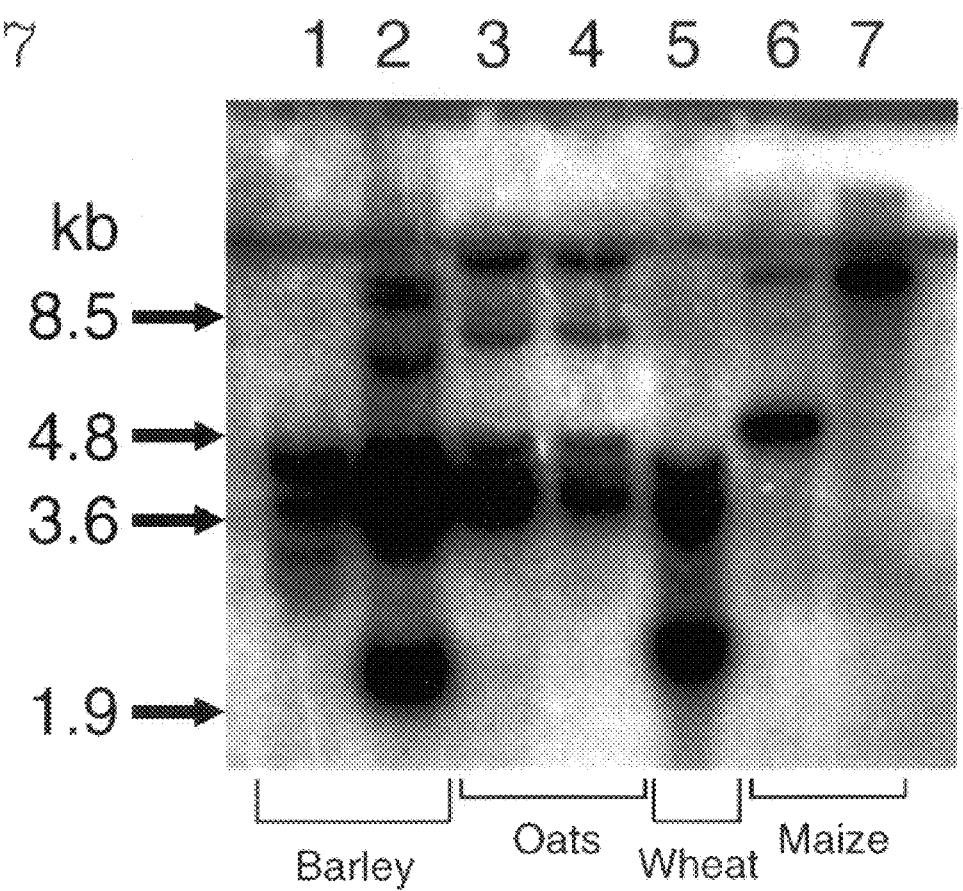

FIG. 7 is a photographic representation of a Southern blot probed with the Mis1 sequence under standard stringency hybridisation conditions [insert conditions]. Each lane contains approximately 10 μg of NcoI-digested total genomic DNA isolated from seedlings of barley cv Franklin (lane 1), barley cv Himalaya (lane 2), oats cv Asceneco (lane 3), oats cv Victoria (lane 4), wheat cv Chinese Spring (lane 5), maize cv Tx303 (lane 6) and maize cv CO159 (lane 7).

DETAILED DESCRIPTION OF THE INVENTION AND PREFERRED EMBODIMENTS

Throughout this specification and claims which follow, unless the context requires otherwise, the word "comprise", or variations such as "comprises" or "comprising", will be understood to imply the inclusion of a stated integer or group of integers but not the exclusion of any other integer or group of integers.

One aspect of the present invention comprises an isolated nucleic acid molecule comprising a sequence of nucleotides which is capable of conferring, activating, enhancing or otherwise increasing the expression of a structural gene in response to a susceptible interaction between a host plant and a fungal pathogen.

Hereinafter the term "susceptible reaction-responsive promoter" or "SRR promoter", or similar term shall be used to define a nucleic acid molecule which is capable of activating or increasing the expression of a structural gene following interaction between a host plant or host plant cell and a fungal pathogen capable of producing a susceptible infection in said host.

Reference herein to a "promoter" is to be taken in its broadest context and includes the cis-regulatory sequences of a classical genomic gene, including the TATA box which is required for accurate transcription initiation, with or without a CCAAT box sequence and additional regulatory elements (i.e. upstream activating sequences, enhancers and silencers) which alter gene expression in response to developmental and/or environmental stimuli, or in a tissue-specific manner. A promoter is usually, but not necessarily, positioned upstream or 5', of a structural gene, the expression of which it regulates. Furthermore, the regulatory elements comprising a promoter are usually positioned within 2 kb of the start site of transcription of the gene.

In the present conk the term "promoter" is also used to describe a synthetic or fusion molecule, or derivative which confers, activates or enhances expression of a structural gene or other nucleic acid molecule, in response to a susceptible interaction between a host and a fungal pathogen. Preferred SRR promoters may contain additional copies of one or more specific regulatory elements to furder enhance expression following fungal infection, and/or to alter the time taken between infection and the enhanced expression, the only requirement being that the SRR promoters are derived from naturally-occurring SRR promoters by standard recombinant techniques.

Generally, an SRR promoter sequence may be subjected to mutagenesis to produce single or multiple nucleotide substitutions, deletions and/or additions. Nucleotide insertional derivatives of the SRR promoter sequence of the present invention include 5' and 3' terminal fusions as well as intra-sequence insertions of single or multiple nucleotides. Insertional nucleotide sequence variants are those in which one or more nucleotides are introduced into a predetermined site in the nucleotide sequence although random insertion is also possible with suitable screening of the resulting product. Deletional variants are characterised by the removal of one or more nucleotides from the sequence.

Substitutional nucleotide variants are those in which at least one nucleotide in the sequence has been removed and a different nucleotide inserted in its place.

The present invention therefore, is directed primarily to the SRR promoter sequences of a classical genomic gene the expression of which is up-regulated in response to a susceptible interaction between a host plant and a fungal pathogen, wherein said SRR promoter sequences confer or activate high-level expression on the gene as a result of said susceptible interaction. It will also be known to those skilled in the art that the activation of gene expression which is observed following a susceptible interaction between a host plant and a fungal pathogen is the result of an interaction between said SRR promoter sequences and any number of cell-specific trans-acting transcription factors. However, the present invention lies in the nucleic acid molecule which comprises said SRR promoter sequences which are particularly useful in conferring high-level expression in a plant cell, on any structural gene to which it is operably linked, wherein the activated expression is in response to a susceptible interaction. For the successful performance of the present invention, it is not necessary that the trans-acting transcription factors are isolated or even known, merely that a plant cell carrying the nucleic acid molecule of the invention produces said factors.

As used herein, the term "structural gene" shall be taken in its broadest context to refer to the transcribed portion of a gene compriun a DNA segment encoding a protein, polypeptide or a portion thereof and includes introns, exons, 5' and 3' untranslated regions of a gene. A structural gene may constitute an uninterrupted coding sequence or it may include one or more introns, bounded by the appropriate plant-functional splice junctions. A structural gene may be a composite or segments derived from a plurality of sources, naturally occurring or synthetic. A structural gene may also encode a fusion protein.

Expression of a structural gene in a cell is regulated by the cis-regulatory sequences to which it is operably linked. The cis-regulatory sequence may be a homologous or heterologous sequence, relative to the structural gene.

A homologous cis-regulatory sequence is one which is operably linked to a particular structural gene in the cell from which it was originally isolated, without any genetic manipulation having been performed thereon. A classical genomic gene, therefore, comprises a homologous cis-regulatory sequence operably linked to a structural gene.

Hereinafter, the term "genetically-linked in vivo to a structural gene" shall be taken to define such homologous cis-regulatory sequences.

A heterologous cis-regulatory sequence is one which is operably linked to a structural gene other than the structural gene to which it would be linked in the absence of human intervention. When a heterologous cis-regulatory sequence is operably linked to a structural gene, the resulting gene is usually termed a "chimeric gene".

Those skilled in the art are aware that the percentage nucleotide sequence identity between homologous genomic genes isolated from different species is highest within the region comprising the structural gene, in particular the coding region thereof Furthermore, although the cis-regulatory sequences of such homologous genomic genes may possess some nucleotide sequence identity, the regions of highest identity are usually limited to short stretches of approximately 6–10 nucleotides in length. However, features of secondary structure in the cis-regulatory sequences as a whole, which may be as long as 2.5 kilobases, may contribute to the overall regulatory activity of any particular cis-regulatory sequence.

A preferred embodiment of the present invention, provides an isolated nucleic acid molecule which is capable of conferring or activating expression on a structural gene in response to a susceptible interaction between a plant cell and a fungal pathogen, wherein said nucleic acid molecule is genetically-linked in vivo to a structural gene which is at least 40% identical to the nucleotide sequence set forth in SEQ ID NO:1 or a complementary strand thereof.

Preferably, the percentage similarity to the sequence set forth in SEQ ID NO: 1 is at least 40%. More preferably, the percentage similarity is at least 60–65%. Still more preferably, the percentage similarity is at least 70–75%. Even more preferably, the percentage similarity as at least 80–90%, including at least 91% or 93% or 95%.

For the purposes of nomenclature, the nucleotide sequence set forth in SEQ ID NO: 1 is the flax Fis1 structural gene. The flax Fis1 genomic gene was is normally expressed in response to a susceptible interaction between the flax plant *Linum usitatissimum* and the flax rust *Melampsora lini* (Table 1), for example between *L.usitatissimum* cv. Hoshangabad and *M. lini* CH5, as described in Example 1 described herein.

In an alternative embodiment, the present invention provides an isolated nucleic acid molecule which is capable of conferring or activating expression on a structural gene in response to a susceptible interaction between a plant cell and a fungal pathogen, wherein said nucleic acid molecule is genetically-linked in vivo to a structural gene which hybridises under at least low stringency conditions to the nucleotide sequence set forth in SEQ ID NO:1 or a complementary strand thereof.

For the purposes of defining the level of stringency, a low stringency is defined herein as being hybridisation and/or a wash carried out in 6×SSC buffer, 0.1% (w/v) SDS at 28° C. Generally, the stringency is increased by reducing the concentration of SSC buffer, and/or increasing the concentration of SDS and/or increasing the temperature of the hybridisation and/or wash. Conditions for hybridisations and washes are well understood by one normally skilled in the art. For the purposes of clarification, (to parameters affecting hybridisation between nucleic acid molecules), reference is found in pages 2.10.8 to 2.10.16. of Ausubel et al. (1987), which is herein incorporated by reference.

More preferably, the present invention provides an isolated nucleic acid molecule which is capable of conferring or activating expression on a structural gene in response to a susceptible interaction between a plant cell and a fungal pathogen, wherein said nucleic acid molecule:
  (i) is genetically-linked in vivo to a structural gene which hybridises under at least low stringency conditions to the nucleotide sequence set forth in SEQ ID NO:1 or a complementary strand thereof; and
  (ii) is genetically-linked in vivo to a structural gene which is at least 40% identical to the nucleotide sequence set forth in SEQ ID NO:1 or a complementary strand thereof.

In a particularly preferred embodiment of the invention, there is provided an isolated nucleic acid molecule which is capable of conferring or activating expression on a structural gene in response to a susceptible interaction between a plant cell and a fungal pathogen, wherein said nucleic acid molecule comprises a sequence of nucleotides of at least 2 kb in length, wherein said sequence includes at the 5'-end the sequence of nucleotides set forth in SEQ ID NO:3 or a homologue, analogue or derivative thereof and at the 3'-end the sequence of nucleotides set forth in SEQ ID NO:4 or a homologue, analogue or derivative thereof.

For the purposes of nomenclature, the sequence shown in SEQ ID NO: 3 and/or SEQ ID NO: 4 relate to the 5' and 3' ends of the Fis1 gene promoter isolated from flax, which is capable of inducing expression of the flax Fis1 gene following infection with flax rust, in a susceptible interaction. The complete nucleotide sequence of the Fis1 promoter, intervening between SEQ ID NO: 3 and SEQ ID NO: 4, is contained in a single 2.2 kb DNA fragment, as described in Example 5 below. The utility of this nucleic acid molecule is exemplified in, but not limited to, the disclosures of Examples 7, 8, and 9 below.

More particularly preferred, the isolated nucleic acid molecule of the invention comprises a sequence of nucleotides which is capable of hybridising under at least low stringency conditions to the SRR promoter sequence of the flax Fis1 gene contained in the microorganism deposited under AGAL Accession No. N96/027087.

Optionally, the isolated nucleic molecule according to these particularly preferred embodiments of the invention is operably linked to a structural gene.

Those skilled in the art will be aware that the expression of any structural gene may be operably linked to the isolated nucleic acid molecule of the invention and as a consequence, the scope of the present invention extends to the use of any structural gene, the expression of which is desired to be increased in response to a susceptible infection by a fungal pathogen.

In a most particularly preferred embodiment of the present invention, the structural gene is a reporter gene selected from the list comprising the bacterial β-glucuronidase (uidA or GUS) and chloramphenicol acetyltransferase genes and the firefly luciferase gene, amongst others or a cytotoxin gene for example the Barnase gene or other gene encoding a ribonuclease enzyme, amongst others.

Cytotoxin genes are well-known to those skilled in the art, as are the methods required for the genetic manipulation and expression in tsgenic plants. Whilst not being bound by any theory or mode of action, wherein the structural gene encodes a cytotoxin molecule, the expression of said structural gene in a plant under the control of the SRR promoter sequences of the invention, will be induced in response to a susceptible interaction between said plant and a fungal pathogen, thereby killing the plant cells at the site of infection and preventing the spread of the fungal pathogen to other sites on the same plant or to neighbouring plants.

The invention further contemplates the use of the SRR promoter sequence of the invention to control the expression of a nucleotide sequence encoding an antisense or a ribozyme molecule, wherein said ribozyme or antisense molecule is capable of inhibiting the expression of a gene required for viability of a plant cell. According to this embodiment, the expression of said antisense or ribozyme molecule will kill the cells which have been infected by an invading fungal pathogen in a susceptible interaction between said pathogen and plant, thereby preventing the continued growth or reproduction of the fungal pathogen in the infected plant, analogous to the mode of action of a cytotoxin gene placed operably under the control of an SRR promoter sequence.

The invention further contemplates the use of the SRR promoter sequence of the invention to control the expression of a nucleotide sequence encoding a ribozyme, antisense or co-supression molecule, wherein said ribozyme, antisense or co-supression molecule is capable of inhibiting the expression of a fungal gene, for example a fungal gene which is required for fungal growth or reproduction. According to this embodiment, the expression of said antisense or ribozyme molecule will prevent the continued growth or reproduction of the fungal pathogen in the infected plant following a susceptible interaction, thereby conferring some degree of protection on the host plant.

Ribozymes are synthetic RNA molecules which comprise a hybridising region complementary to two regions, each of at least 5 contiguous nucleotide bases in the target mRNA. In addition, ribozymes possess highly specific endoribonuclease activity, which autocatalytically cleaves the target mRNA. A complete description of the function of ribozymes is presented by Haseloff and Gerlach (1988) and contained in International Patent Application No. WO89/05852. The present invention extends to ribozymes which target an mRNA encoding an SR gene product.

Antisense molecules are nucleic acid molecules which are capable of forming a double-stranded duplex with an mRNA molecule, thereby preventing its translation into a polypeptide.

Co-suppression is the reduction in expression of an endogenous gene that occurs when one or more copies of said gene, or one or more copies of a substantially similar gene are introduced into the cell.

The present invention is particularly directed to an SRR promoter, preferably the flax Fis1 gene promoter, that induces host gene expression in a susceptible interaction between the flax plant *Linum usitatissimum* and the flax rust *Melampsora lini*. Examples of flax SRR promoter sequences that induce gene expression in a susceptible interaction with a flax rust, include, but are not limited to, the flax Fis1 gene promoter sequence.

The subject invention clearly contemplates other sources of SRR promoter sequences, such as but not limited to the cereal plants wheat, maize, barley, rye, oats and rice amongst others. According to this embodiment of the present invention, non-limiting examples of potential sources of SRR promoter sequences and the susceptible host/rust interactions in which they induce gene expression, is presented in Table 1.

In a particularly preferred embodiment, the present invention extends to the SRR promoter sequence from the maize Mis1 gene which is induced in the susceptible interaction between maize and the maize rust *Puccinia sorghi*, in particular between maize and *P. sorghi* race 1.

TABLE 1

Examples of susceptible interactions between plant species and their respective fungal pathogens

| PATHOGEN | HOST PLANT |
|---|---|
| *Puccinia graminis* | wheat, barley and rye |
| *Puccinia striformis* | wheat and rye |
| *Puccinia recondita* | rye and wheat |
| *Puccinia hordei* | barley |
| *Puccinia coronata* | oat |
| *Puccinia sorghi* | maize |
| *Puccinia polysora* | maize |
| *Puccinia purpurea* | sorghum |
| *Puccinia sacchari* | sugar cane |
| *Puccinia kuehnii* | sugar cane |
| *Puccinia arachidis* | peanut |
| *Puccinia stachmanii* | cotton |
| *Uromyces striatus medicaginis* | alfalfa |
| *Uromyces phaseoli* | *phaseolus* beans |
| *Hemileia vastatrix* | coffee rust |

TABLE 1-continued Examples of susceptible interactions between plant species and their respective fungal pathogens

| PATHOGEN | HOST PLANT |
|---|---|
| *Melampsora lini* | flax |
| *Gymnosporangium juniperi-virginianae* | cedar and apple |
| *Cronartium ribicola* | white pine |
| *Cronartium fusiforme* | loblolly and slash pine |

The genetic sequences comprising an SRR promoter sequence may correspond to the naturally-occurring sequence, or may differ by one or more nucleotide substitutions, deletions and/or additions.

It is understood in the art that modifications may be made to the structural arrangement of specific enhancer and promoter elements of the SRR promoter molecule described herein without destroying the improved enhancing activity of gene expression. For example, it is contemplated that a substitution may be made in the choices of plant-expressible enhancer and promoter elements without significantly affecting the function of the recombinant SRR promoter molecule of this invention. Further, it is contemplated that nucleotide sequences homologous to the active enhancer elements utilized herein may be employed advantageously, either as a substitution or an addition to the recombinant promoter construct for improved gene expression in plant cells, in response to infection of said plant cell with a rust fungus, in a susceptible interaction. It will also be understood by one normally skilled in the art that the function of an SRR promoter sequence also results from the arrangement, orientation and spacing of the difference enhancer elements with respect to one another, and with respect to the position of the TATA box. Accordingly, the present invention extends to SRR promoter sequences and any functional promoters, derivatives, parts, fragments, homologues, or analogues thereof, or non-functional molecules which are at least useful as, for example genetic probes in the isolation of similar sequences, or primer sequences in the enzymatic or chemical synthesis of said gene, or in the generation of immunologically interactive recombinant molecules.

The SR structural genetic sequence is particularly useful in isolating the homologous SRR promoter to which it is operably linked in vivo. Thus, by using the SR structural gene as a probe, or to design PCR primers, it is possible to isolate SRR promoter sequences which fall within the scope of the present invention. For example, the inventors have used the Fis1 promoter sequence to isolate the corresponding maize Mis1 gene, via the Fis1 structural gene intermediate, as described in Example 11 incorporated herein.

The present invention clearly extends to a genetic sequence comprising at least, the coding region of a gene, hereinafter defined as a "susceptible reaction structural gene", or "SR structural gene" which, in its native state is expressed in response to a susceptible interaction between a host and a rust fungus. Reference herein to "SR structural genes" is to be taken in its broadest context and includes:

(i) a classical genomic SR structural gene consisting of transcriptional and/or translational regulatory sequences and/or a coding region and/or non-translated sequences (i.e. introns, 5'- and 3'- untranslated sequences); or (ii) mRNA or cDNA corresponding to the coding regions (i.e. exons) and 5'- and 3'- untranslated sequences of the gene.

The term "SR structural gene" is also used to describe synthetic or fusion molecules encoding all or part of a functional product. Preferred SR structural genes may be derived from a naturally-occuring SR structural gene by standard recombinant techniques. Generally, an SR structural gene may be subjected to mutagenesis to produce single or multiple nucleotide substitutions, deletions and/or additions. Nucleotide insertional derivatives of the SR structural gene of the present invention include 5'and 3'terminal fusions as well as intra-sequence insertions of single or multiple nucleotides. Insertional nucleotide sequence variants are those in which one or more nucleotides are introduced into a predetermined site in the nucleotide sequence although random insertion is also possible with suitable screening of the resulting product Deletional variants are characterised by the removal of one or more nucleotides from the sequence. Substitutional nucleotide variants are those in which at least one nucleotide in the sequence has been removed and a different nucleotide inserted in its place. Such a substitution may be "silent" in that the substitution does not change the amino acid defined by the codon. Alteratively, substituents are designed to alter one amino acid for another similar acting amino acid, or amino acid of like charge, polarity, or hydrophobicity.

Accordingly, a second aspect of the present invention is directed to an isolated nucleic acid molecule which comprises an SR structural gene as hereinbefore defined.

Preferably, said SR structural gene comprises a sequence of nucleotides which which corresponds or is complementary to the sequence as set forth in SEQ ID NO: 1, or having at least about 40%, more preferably at least about 55%, still more preferably at least about 65%, yet still more preferably at least about 75–80% and even still more preferably at least about 85–95% nucleotide similarity to all, or a homologue, analogue or derivative thereof.

In an alternative embodiment of this aspect of the invention, said nucleic acid molecule is capable of hybridising under at least low stringency conditions to the nucleic acid molecule set forth in SEQ ID NO: 1, or to a complementary strand thereof.

According to this aspect, said SR structural gene encodes, or is complementary to a sequence encoding, a polypeptide which is expressed in response to a susceptible interaction between a host and a rust fungus.

In a particularly preferred embodiment, said SR structural gene is the flax Fis1 gene set forth in SEQ ID NO:1 which encodes the amino acid sequence set forth in SEQ ID NO:2 or a homologue, analogue or derivative thereof.

The SR structural gene is particularly useful as a molecular tag in the identification of homologous nucleic acid molecules which are expressed in response to a susceptible infection by a fungal pathogen. This attribute of the SR structural gene arises from the fact that it is normally expressed under the control of an SRR promoter sequence, for example the flax Fis1 promoter sequence and, as a consequence, expression of the homologous sequence is up-regulated in the cell in response to said fungal infection. In this regard, the SR structural gene is useful in the detection of increased expression of any SR structural gene to which it is capable of hybridising or to which at least 10 contiguous nucleotides derived therefrom are capable of hybridising under at least low stringency conditions.

Accordingly, the present invention provides, in a further aspect, a method of detecting infection of a plant by a fungal pathogen which is capable of forming a susceptible interaction therewith, said method comprising the step of detecting increased expression of an SR structure gene in said plant.

Preferably, said step of detecting increased expression is performed by contacting a nucleic acid molecule derived from said plant with a second nucleic acid molecule comprising the nucleotide sequence set forth in SEQ ID NO:1 or a fragment of at least 10 contiguous nucleotides in length derived therefrom for a time and under conditions sufficient to allow a double-stranded nucleic acid molecule to form.

More preferably, the second nucleic acid molecule is labelled with a reporter molecule such as a radioactive or biotinylated molecule, enzyme, antibody or any other molecule which can be assayed by known methods. According to this embodiment, the amount of bound nucleic acid molecule formed during the hybridisation step can be assayed by determining the amount of bound reporter molecule.

The method according to this aspect of the invention is particularly applicable to the detection of an infection in a plant by a fungal pathogen, wherein said plant and respective fungal pathogen is selected from the list of pathogen-:host plant combinations set forth in Table 1.

The SRR promoter sequence and/or the SR structural genetic sequence of the present invention are further useful in the isolation of said related SRR promoter sequences and SR structural genes from other plants. Where the level of nucleotide sequence identity between the SRR promoter sequence of the invention and the related sequence is sufficiently high, it is possible to use the SRR promoter directly as a hybridisation probe. However, where there is insufficient nucleotide sequence similarity between the SRR promoter of the invention and a functionally-related SRR promoter, the related SR structural gene and/or the genomic clone equivalents thereof may be isolated first and used in turn to isolate the related SRR promoter sequence.

According to this embodiment, there is contemplated a method for identifying a related SRR promoter sequence, or SR structural genetic sequence, said method comprising contacting genomic DNA, or mRNA, or cDNA, or parts of fragments thereof, or a source thereof, with a hybridisation-effective amount of a first SRR promoter sequence or first SR structural gene, or a part thereof, and then detecting said hybridisation.

The related SRR promoter sequence or SR structural genetic sequence may be in a recombinant form, in a virus particle, bacteriophage particle, yeast cell, animal cell, or a plant cell. Preferably, the related genetic sequence originates from *Triticum aestivum* or similar plant such as barley, rye, oats, maize or rice and/or wild varieties and/or hybrids or derivatives and/or ancestral progenitors of same. In addition, the related genetic sequence may be bound to a support matrix, for example nylon, nitrocellulose, polyacrylamide, agarose, amongst others.

Preferably, the first SRR promoter sequence, or first SR structural genetic sequence, is from flax, or other plant such as wheat, barley, rye, oats, maize or rice.

Preferably, the SR stgral gene comprises a sequence of nucleotides which is capable Aof hybridising under at least low stringency conditions to the sequence set forth in SEQ ID NO:1 or a complement, homologue, analogue or derivative thereof.

In a particularly preferred embodiment, the SRR promoter sequence comprises a sequence of nucleotides of at least 2 kb in length, wherein said sequence includes at the 5'-end the sequence of nucleotides set forth in SEQ ID NO:3 or a homologue, analogue or derivative thereof and at the 3'-end the sequence of nucleotides set forth in SEQ ID NO:4 or a homologue, analogue or derivative thereof.

More particularly preferred, the fist SRR promoter comprises a sequence of nucleotides which is capable of hybridising under at least low stringency conditions to the SRR promoter sequence of the flax Fis1 gene contained in the microorganism deposited under AGAL Accession No. N96/027087.

Preferably, the SRR promoter sequence, or SR structural gene is labelled with a reporter molecule capable of producing an identifiable signal (eg. a radio isotope Such as $^{32}P$, or $^{35}S$, or a biotinylated molecule) to facilitate its use as a hybridisation probe in the isolation of related SRR promoter sequences and SR structural genes.

For the purposes of defining the level of stringency, a low stringency is defined herein as being a hybridisation and/or a wash carried out in 6×SSC buffer, 0.1% (w/v) SDS at 28° C. Generally, the stringency is increased by reducing the concentration of SSC buffer, and/or increasing the concentration of SDS and/or increasing the temperature of the hybridisation and/or wash. Conditions for hybridisations and washes are well understood by one normally skilled in the art. For the purposes of clarification, (to parameters affecting hybridisation between nucleic acid molecules), reference is found in pages 2.10.8 to 2.10.16. of Ausubel et al. (1987), which is herein incorporated by reference.

Alternatively, an SR structural and/or the genomic clone equivalent thereof which is related to the flax Fis1 structural gene set forth in SEQ ID NO:1 may be isolated by amplification using the polymerase chain reaction (PCR) employing oligonucleotide primers derived from SEQ ID NO:1. The polymerase chain reaction procedure used in the present invention involves hybridising a nucleic acid primer molecule of at least 10 nucleotides in length to a nucleic acid "template molecule", said template molecule herein defined as a SRR promoter sequence, or SR structural genetic sequence, or a functional part thereof, or its complementary sequence. A related SRR promoter may subsequently be isolated, either directly from said genomic clone equivalent or alternatively, by hybridisation using the related SR structral gene as a hybridisation probe. Such methods are well-known to those skilled in the art.

The nucleic acid primer molecule or molecule effective in hybridisation may be contained in an aqueous mixture of other nucleic acid primer molecules or in a substantially pure form.

In a preferred embodiment, the nucleic acid primer molecule comprises at least 10 contguous nucleotides in length derived from the from a flax Fis1 sequence set forth in any one of SEQ ID Nos: 1, 3, 4, 5, 6 or 7. For the purposes of nomenclature, SEQ ID NOs: 5–7 each comprise a degenerate sequence of nucleotides which encode or are complementary to a sequence of nucleotides which encode an SR gene product motif set forth in Table 2.

More preferably, said oligonucleotide molecule comprises a sequence of nucleotides substantially the same as the nucleotide sequence set forth in SEQ ID NO:5, SEQ ID NO:6 or SEQ ID NO:7 or a homologue, analogue or derivative thereof.

The nucleic acid template molecule may be in a recombinant form, in a virus particle, bacteriophage particle, yeast cell, animal cell, or a plant cell. Preferably, the related genetic sequence originates from *Triticum aestivum* or similar plant such as barley, rye, oats, maize, or rice and/or wild varieties and/or hybrids or derivatives and/or ancestral progenitors of same.

In a particularly preferred embodiment, the present invention provides an oligonucleotide molecule which is useful as a hybridisation probe or PCR primer derived from the nucleotide sequence set forth in any one of SEQ ID Nos: 1, 3 or 4 or a homologue, analogue or derivative thereof.

More preferably, said oligonucleotide molecule comprises a sequence of nucleotides substantially the same as the nucleotide sequence set forth in SEQ ID NO:5, SEQ ID NO:6 or SEQ ID NO:7 or a homologue, analogue or derivative thereof.

A further aspect of the present invention is directed to a genetic construct comprising an SRR promoter sequence or a homologue, analogue or derivative thereof as hereinbefore defined.

The SRR promoter seduce or a functional derivative, part, fragment, homologue, or analogue thereof may be used to regulate the expression of a heterologous structural gene such as a reporter gene or gene encoding a cytotoxin or alternatively, it may regulate the expression of a nucleic acid molecule which encodes a ribozyme or antisense molecule.

Placing a structural gene under the regulatory control of an SRR promoter means positioning the structural gene such that the expression of the gene is controlled by these promoter sequences. Promoters are generally positioned 5' (upstream) to the genes that they control. In the construction of heterologous promoter/structural gene combinations it is generally preferred to position the promoter at a distance from the gene transcription start site that is approximately the same as the distance between that promoter and the gene it controls in its natural setting, i.e., the gene from which the promoter is derived. As is known in the art, some variation in this distance can be accommodated without loss of promoter function. Similarly, the preferred positioning of a regulatory sequence element with respect to a heterologous gene to be placed under its control is defined by the positioning of the element in its natural setting, i.e., the genes from which it is derived. Again, as is known in the art and demonstrated herein with multiple copies of reglatory elements, some variation in this distance can occur.

Preferred reporter genes include the β-glucuronidase gene, chloramphenicol acetyl transferase gene or the firefly luciferase gene, amongst others. Preferred cytotoxcin genes include the bamase gene or other ribonuclease gene.

The cytotoxin gene or ribozyme or antisense molecule may be any of those discussed supra which, when produced in a plant cell either kills, disables or repels a fungus, or kills or at least significantly alters host cell metabolism to limit spread and/or development of said fungus.

Preferably, the SRR promoter sequence comprises a sequence of nucleotides of at least 2 kb in length, wherein said sequence includes at the 5'-end the sequence of nucleotides set forth in SEQ ID NO:3 or a homologue, anaologue or derivative thereof and at the 3'-end the sequence of nucleotides set forth in SEQ ID NO:4 or a homologue, analogue or derivative thereof.

More particularly preferred, the first SRR promoter comprises a sequence of nucleotides which is capable of hybridising under at least low stringency conditions to the SRR promoter sequence of the flax Fis1 gene contained in the microorganism deposited under AGAL Accession No. N96/027087.

In a most particularly preferred embodiment, the genetic construct of the present invention comprises the GUS reporter gene operably linked to the flax Fis1 promoter sequence, for example in the pFisGUS52 genetic construct set forth in FIG. 2a and deposited under AGAL Accession No. N961027087.

A further aspect of the present invention contemplates a transgenic plant such as a crop plant, carrying a non-endogenous SRR promoter sequence and/or an SR structural genetic sequence as hereinbefore defined. Preferably the SRR promoter sequence or the SR structural genetic sequence are essentially identical to, or derived from, the flax Fis1 nucleotide sequence.

Preferably, the transgenic plant is a flax plant. More preferably, the transgenic plant is one or more of the following: flax, wheat, barley, oats, rye, rice, maize, amongst others. Additional species arc not excluded.

In a most particularly preferred embodiment, the transgenic plant is a flax plant which has been transformed with the genetic construct deposited under AGAL Accession No. N96/027087.

Methods for the transformation of plant tissue are well-known to those skilled in the art. The technique used for a given plant species or specific type of plant tissue depends on the known successful techniques. Means for introducing recombinant DNA into plant tissue include, but are not limited to, transformation (Paszowski et a, 1984), electroporation (Fromm et al., 1985), or microinjection of the DNA (Crossway et al., 1986) or T-DNA-mediated transfer from Agrobacterium to the plant tissue. Representative T-DNA vector systems are described in the following references: An et al. (1985); Herrera-Estrella et al. (1983 a,b); Herrera-Estrella et al. (1985). Once introduced into the plant tissue, the expression of the structural gene may be assayed in a transient expression systems, or it may be determined after selection for stable integration within the plant genome. Techniques are known for the in vitro culture of plant tissue, and for regeneration into whole plants. Procedures for transferring the introduced gene from the originally transformed plant into commercially useful cultivars are known to those skilled in the art.

The present invention extends to the progeny derived from said transgenic plant.

A further aspect of the invention provides for the expression of an SR structaral gene in a suitable host (eg a prokaryotic or eukaryotic cell) to produce a fill-length or non-full-length recombinant SR gene product.

Preferably the SR gene product further contains two, still more preferably three and even still more preferably four of the amino acid sequence motifs comprising the list set forth in Table 2. Preferably, the SR gene product has a sequence that is at least 40% identical to the amino acid sequence set forth in SEQ ID NO: 2 or a homologue, analogue or derivative thereof In a particularly preferred embodiment, the SR gene product comprises a sequence of amino acids which is substantially the same as the flax Fis1 polypeptide sequence set forth in SEQ ID NO:2.

The present invention extends also to a synthetic peptide fragment of an SR gene product, preferably the SR gene product set forth in SEQ ID NO: 2.

TABLE 2

SR gene product motifs

| MOTIF | AMINO ACID SEQUENCE |
|---|---|
| GPL | WPFGPVAIITPFNFPLEIPVLQLMGALYMGNKPLLKV (SEQ ID NO: 8) |
| GSG | RMTLFTGSSRVAEKLALDLKGRIRIKLED (SEQ ID NO: 9) |
| GQG | DAYACSGQKCSAQSILFMHE (SEQ ID NO: 10) |
| EEP | NYELVTKEIFGPFQVVTEYKNSQLPMVLEA (SEQ ID NO: 11) |

In an alternative embodiment, the present invention extends to an SR gene product comprising an amino acid sequence motif which is at least 40% similar, or preferably 40–60% similar, or more preferably 60–90% similar, or still more preferably 90–100% similar, to an amino acid sequence motif selected from the list set forth in Table 2.

The present invention extends further to a recombinant gene product comprising an amino acid sequence motif selected from the list set forth in Table 2 in any relative combination, or frequency, or a functional derivative thereof, having at least 40% similarity to same.

According to this aspect, the recombinant SR gene product of the present invention, or a functional derivative thereof, may be used to pruce immunologically interactive molecules, such as antibodies, or functional derivatives thereof, the only requirement being that the recombinant products are immunologically interactive with antibodies to all or part of an SR gene product.

Antibodies to a recombinant SR gene product are particularly useful in the screening of plants for the presence of said gene product. Another aspect of the present invention is, therefore, directed to antibodies to a recombinant SR gene product or part or fragment thereof. Such antibodies may be monoclonal or polyclonal and may be selected from natually occumng antibodies to an SR gene product or may be specifically raised to a recombinant SR gene product. In the case of the latter, the SR gene product may first need to be associated with a carrier molecule. Alternatively, fragments of antibodies may be used such as Fab fragments. Furthermore, the present invention extends to recombinant and synthetic antibodies and to antibody hybrids. A "synthetic antibody" is considered herein to include fragments and hybrids of antibodies. The antibodies and/or the recombinant SR gene products of the present invention are particularly useful for the immunological screening of SR gene products in various plants, leading to the isolation of related SRR promoter sequences and SR structural genes.

In one embodiment, specific antibodies are used to screen for SR gene products in plants. Techniques for the assays contemplated herein are known in the art and include, for example, sandwich assays and ELISA.

It is within the scope of this invention to include any second antibodies (monoclonal, polyclonal or fragments of antibodies) directed to the first mentioned antibodies discussed above. Both the first and second antibodies may be used in detection assays or a first antibody may be used with a commercially available anti-immunoglobulin antibody. An antibody as contemplated herein includes any antibody specific to any region of a recombinant SR gene product.

Both polyclonal and monoclonal antibodies are obtainable by immunisation with a recombinant SR gene product and either type is utilisale for immunoassays. The methods of obtaining both types of sera are well known in the art. Polyclonal sera are less preferred but are relatively easily prepared by injection of a suitable laboratory animal with an effective amount of recombinant SR gene product, or antigenic or immunointeractive parts thereof, collecting serum from the animal and isolating specific sera by any of the known immunoadsorbent techniques. Although antibodies produced by this method are utilisable in virully any type of immunoassay, they are generally less favoured because of the potential heterogeneity of the product.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitised against the immunogenic preparation can be done by techniques which are well known to those who are skilled in the art (see, for example, Douillard and Hoffman, 1981; Kohler and Milstein, 1975; Kohler and Milstein, 1976).

The presence of an SR gene product in a plant or more commonly plant extract may be accomplished in a number of ways such as by Western blotting and ELISA procedures. A wide range of immunoassay techniques are available as can be seen by reference to U.S. Pat. Nos. 4,016,043, 4,424,279 and 4,018,653. These, of course, includes both single-site and two-site or "sandwich" assays of the non-competitive types, as well as in the traditional competitive binding assays. These assays also include direct binding of a labelled antibody to a target.

Sandwich assays are among the most useful and commonly used assays and are favoured for use in the present invention. A number of variations of the sandwich assay technique exist, and all are intended to be encompassed by the present invention. Briefly, in a typical forward assay, an unlabelled antibody is immobilised on a solid substrate and the sample to be tested brought into contact with the bound molecule. After a suitable period of incubation, for a period of time sufficient to allow formation of an antibody-antigen complex, a second antibody specific to the antigen, labelled with a reporter molecule capable of producing a detectable signal is then added and incubated, allowing time sufficient for the formation of another complex of antibody-antigen-labelled antibody. Any unreacted material is washed away, and the presence of the antigen is determined by observation of a signal produced by the reporter molecule.

In this case, the first antibody is raised to a recombinant SR gene product and the antigen is an SR gene product in a plant.

The results may either be qualitative, by simple observation of the visible signal, or may be quantitated by comparing with a control sample containing known amounts of hapten. Variations on the forward assay include a simultaneous assay, in which both sample and labelled antibody are added simultaneously to the bound antibody. These techniques are well known to those skilled in the art, including any minor variations as will be readily apparent. In accordance with the present invention the sample is one which might contain an SR gene product and include crude or purified plant extract such as extracts of leaves, roots and stems.

In the typical forward sandwich assay, a first antibody raised against a recombinant SR gene product is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking, covalent binding or physically adsorption, the polymer-antibody complex is washed in preparation for the test sample. An aliquot of the sample to be tested is then added to the solid phase complex and incubated for a period of time sufficient (e.g. 2–40 minutes) and under suitable conditions (e.g. 25° C.) to allow binding of any antigen present in the sample to the antibody. Following the incubation period, the reaction locus is washed and dried and incubated with a second antibody specific for a portion of the first antibody. The second antibody is linked to a reporter molecule which is used to indicate the binding of the second antibody to the hapten.

An alternative method involves immobilising the target molecules in the biological sample and then exposing the immobilised target to specific antibody which may or may not be labelled with a reporter molecule. Depending on the amount of target and the strength of the reporter molecule signal, a bound target may be detected by direct labelling with the antibody. Alternativly, a second labelled antibody, specific to the first antibody is exposed to the target-first antibody complex to form a target-first antibody-second antibody tertiary complex. The complex is detected by the signal emitted by the reporter molecule.

By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclides containing molecules (i.e. radioisotopes) and chemiluminescent molecules.

In the case of an enzyme immunoassay, an enzyme is conjugated to the second antibody, generally by means of glutaraldehyde or periodate. As will be readily recognised, however, a wide variety of different conjugation techniques exist which are readily available to the skilled artisan. Commonly used enzymes include horseradish peroxidase, glucose oxidase, beta-galactosidase and alkaline phosphatase, amongst others. The substrates to be used with the specific enzymes are generally chosen for the production, upon hydrolysis by the corresponding enzyme, of a detectable colour change. Examples of suitable enzymes include alkaline phosphatase and peroxidase. It is also possible to employ fluorogenic substrates which yield a fluorescent product rather than the chromogenic substrates noted above. In all cases, the enzyme-labelled antibody is added to the first antibody-hapten complex, allowed to bind, and then the excess reagent is washed away. A solution containing the appropriate substrate is then added to the complex of antibody-antigen-antibody. The substrate will react with the enzyme alinked to the second antibody, giving a qualitative visual signal, which may be further quantitated, usually specthotometrically, to give an indication of the amount of hapten which was present in the sample. The term "reporter molecule" also extends to use of cell agglutination or inhibition of agglutination such as red blood cells on latex beads, and the like.

Alternately, fluorescent compounds, such as fluorescein and rhodamine, may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic colour visually detectable with a light microscope. As in enzyme immimoassays (EIA), the fluorescent labelled antibody is allowed to bind to the first antibody-hapten complex After washing off the unbound reagent, the remaining tertiary complex is then exposed to the light of the appropriate wavelength the fluorescence observed indicates the presence of the hapten of interest. Immunofluorescene and EIA techniques are both very well established in the art and are particularly preferred for the present method. However, other reporter molecules, such as radioisotope, chemiluminescent or bioluminescent molecules, may also be employed.

Microorganism Deposits

A host *Escherichia coil* cell transformed with a vector designated pFisGUS52 comprising the flax Fis1 gene promoter driving GUS reporter gene expression has been deposited in accordance with the Budapest Treaty on the International Recognition of the Deposit of Microorganisms for the Purposes of Patent Procedure, with the Australian Government Analytical Laboratories P.O. Box 385 Pymble, New South Wales 2073, Australia on May 3, 1996 under Accession No. N96/027087.

Single letter and three letter abbreviations used for amino acid residues in the specification are defined in Table 3.

TABLE 3

| Amino Acid | Three-letter Abbreviation | One-letter Symbol |
| --- | --- | --- |
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalamine | Phe | F |
| Proline | Pro | P |
| Serine | Ser | S |
| Threonine | Thr | T |
| Tryptophan | Trp | W |
| Tyrosine | Tyr | Y |
| Valine | Val | V |

EXAMPLE 1

Plant Material and Rust Strains

All susceptible infections with the rust strain CH5 were done on 12-day old flax seedlings (*Linum usitatissimum* cv. Hoshangabad). Fresh spores were sprinkled over the seedlings and allowed to germinate overnight at 20° C., in a humidified environment. For resistant infections, flax seedlings (*L. usitatissimum* cv. Forge, Ellis et al., 1992) was used as the host for rust strain CH5.

EXAMPLE 2

Isolation of RNA and DNA from Flax Seedlings

Flax seedling leaves were ground in liquid nitrogen and suspended in 20 mM TRIS pH 7.5, 100 mM NaCl, 2.5 mM EDTA, 1% SDS, 0.5% 2-mercaptoethanol (5ml/g). Protein was removed by emotion three times with phenol:chloroform:isoamyl alcohol. Total nucleic acid was precipitated with an equal volume of iso-propanol, collected by centifgation and re-suspended in TE (maniatis et al., 1982). The RNA was precipitated from the DNA and contaminating carbohydrates by the addition of solid NaCl to a final concentration of 3M NaCl. DNA was xracted in a similar procedure but after the precipitation of total nucleic acid the DNA was purified on a CsCl density gradient (Maniatis et al., 1982).

EXAMPLE 3

Isolation of a Susceptible Response cDNA

Total RNA was extracted from flax leaves (cv. Hoshangabad) infected heavily with rust spores, as described in Examples 1 and 2. Poly A+RNA was purified on oligo d(T) magnetic beads and reverse-transcribed using an oligo d(T) primer molecule containing a NotI restriction site as the primer for cDNA synthesis. The cDNA was enriched for sequences specific to the rust-infected leaves, by substrative hybridisation to 10 μg of biotinylated polyA+ RNA from uninfected flax leaves. The subtraction procedure was carried out three times, after which the purified cDNA sequences were tailed at the 3'-termini using dATP and terminal transferase (BRL, Gainsville, Fla. USA). The cDNA sequences were subsequently amplified in a polymerase chain reaction and cloned into the plasmid pGEM5 (Promega, Madison Wis. USA) as NotI DNA fragments.

Seven unique cDNA clones were isolated, which were expressed at low levels in uninfected flax leaves. The expression of one cDNA clone, pFIS1, was induced by infection of flax leaves with rust spores in a susceptible infection and was therefore deemed to correspond to an SR structural genetic sequence. The nucleotide sequence of the Fis1 structural gene is set forth in SEQ ID NO:1.

EXAMPLE 4

THE SR Structural Gene Fis1 is a Flax Genetic Sequence

To demonstrate that the cDNA pFIS1, of the foregoing Example 3, is a genetic sequence derived from the flax plant and not from the flax rust, DNA was isolated from both the flax and the rust organisms and hybridised to the pFIS1 cDNA insert.

As shown in FIG. 1, pFIS1 hybridised to flax DNA and not to rust DNA confirming that pFIS1 is from a flax gene defined as fis1. Tne hybridisation pattern was simple, suggesting fis1 is a low copy number gene. Two hybridisimg bands were present in both HindIII and BglII digestions. Since the pFIS1 probe used does not contain these restriction enzyme recognition sites, these data are consistent with there being two genes homologous to pFIS1.

EXAMPLE 5

Isolation of the Fis1 Gene Promoter

A genomic clone containing a 2.2 kb SRR promoter fragment was isolated, using the SR structural genetic sequence of the foregoing Examples 3 and 4 as a hybridisation probe. A lambda genomic library was screened using a 5' end probe from the FIS1 cDNA, the NruI/AccI fragment. Genomic clones which hybridised to this 5' end probe were screened based on their restriction digestion pattern with the enzymes Bgl II and Acc I, (there is an Acc I site at position 295 and a Bgl II site at position 1143 in FIS1 cDNA) and the size of the inserts was compared with that obtained when genomic DNA is cut with Bgl II and Acc I. In genomic DNA, there are two fragments that hybridise with the 5' end probe. The 6 genomic clones that were isolated were grouped into two classes based on the restriction digestion pattern with Bgl II and Acc I. The Bgl II fragments containing hybridising DNA were subcloned into a plasmid vector, (Bluescript) and partial sequence data was obtained from each end. Sequence analysis (from the internal Bgl II site) showed that of the two classes of clones, one was 100% similar to the Fis1 cDNA and the other was only about 95% similar. One of those that was 100% similar was used to construct the promoter fusion with the $E.$ $coli$ β-glucuronidase (GUS) gene as described in Example 7 below. The 5' end and 3' end of the Fis1 gene promoter have been sequenced and the nucleotide sequences are set forth in SEQ ID NO: 3 and SEQ ID NO: 4, respectively.

EXAMPLE 6

Nucleotide Sequence Analysis of the Fis1 Genetic Sequences

DNA was sequenced using the Applied Biosystems double stranded DNA sequencing system (Perkin-Elmer, CA, USA). The sequence was analyzed with the Wisconsin GCG package.

Sequence data of the Fis1 cDNA clone pFIS1 reveals an ATG translation start codon at nucleotide 57 in SEQ ID NO: 1. The longest open reading frame (1653 base pairs) found in pFIS1 had 551 amino acids and a predicted molecular weight of approximately 61 kDa.

A search of the Blocks (v6.0) and Prosite database (Henikoff and Henikoff, 1991) of conserved protein sequence motifs revealed that the amino acid sequence of the Fis1 gene product, set forth in SEQ ID NO: 2, has several conserved sequence motifs that are found in aldehyde dehydrogenases (Hempel et al., 1993). Amino acids residues surrounding Cys-332 match the consensus for the cysteine active site found in all aldehyde dehydrogenases (Henikoff and Henikoff, 1991). In addition to this "cysteine active site", the Blocks search revealed three other sequence motifs that are also found in aldehyde dehydrogenases, and are shown in Table 2. The search of the Blocks database gave an estimate p-value p<7.8e-07 and a "shuffled" score of 1450= 99.86th percentile for the aldehyde dehydrogenase blocks. The first such amino acid sequence identified is between Gly-193 and Lys-226 known as the GPL motif. The second is the GSG motif between Phe-276 and Ala-282. The third motif between Lys435 and Pro-550 is the EEP motif. A comparison of FIS1 GPL motif sequence with the corresponding region of the $E.$ $coli$ proline dehydrogenase polypeptide showed that from amino acids 192 to 225 there is 50% similarity (36/71 amino acids) between the two sequences. Similarly, there is 65% and 50% similarity in GSG motif and the REP motif,m respectively, between flax FIS1 and the $E.$ $coli$ proline dehydrogenase polypeptide. The relative size of FIS1 protein is also consistent with it being an aldehyde dehydrogenase. A glutamic acid containing sequence, known as the FGS motif which is present in aldehyde dehydrogenases except the subclass of methylmalonate-semialdehyde dehydrogenases was also missing from FIS1.

EXAMPLE 7

Expression of a Fis1 /Gus Genetic Construct in Transgenic Plants

The bacterial β-glucoronidase structural gene was placed operably under control of the SRR promoter sequence, corresponding to the flax Fis1 gene promoter of the foregoing Examples 5 and 6, as shown in FIG. 2a.

The binary plant transformation vector, pBI101 was used as the source of the GUS gene. The pBI101 plasmid was cut with Bam HI and then filled in with $E.$ $coli$ DNA polymerise, Klenow fragment, to form a blunt end. This blunt end was then used in a digestion with Xba I to give a plasmid with a 5' Xba I end and a 3' blunt end (the GUS end). The 2 kb 5' region of the Fis1 gene from the Nru I site in the gene, to the Xba I in the bluescript vector, was there ligated into the pBI101 plasmid. This resulted in the addition of 43 amino acid from the Fis1 coding region being added to the GUS protein. The resultant plasmid, designated pFisGUS52 and shown in FIG. 2($a$) has been deposited under AGAL Accession No. N96/027087.

The genetic construct was then introduced into flax plants by Agrobacterium-mediated transformation procedures known to those skilled in the art. Transgenic plants were selected on kanamycin containing media. The regenerated plants were tested for GUS activity by infiltrating leaves in 10 mM phosphate buffer, 0.5 mM K ferricyanide, 0.5 mM K ferrocyanide, 1 mM X-glucuronide, overnight at 37° C. Leaves of T2 transgenic plants were infected with rust for 4 days and then GUS stained to reveal the pattern of expression. As shown in FIG. 2(b), the GUS gene is expressed in plant cells infected in a susceptible interaction with a fungal pathogen. Uninfected cells do not show detectable GUS gene expression.

EXAMPLE 8

Analysis of Flax Fis1 Gene Expression During a Susceptible Rust Infection

Flax RNA was electrophoresed using standard denaturing formaldehyde gels (Mania tis et al., 1982) to separate 10 or 20 µg of total RNA. The RNA was then transferred with 20×SSC to Hybond N membranes (Amesham International, UK). DNA probes were labelled with [α-$^{32}$P]dCTP using the Megaprime system (Amersham). The amounts of $^{32}$P-labelled probe hybridizing to the filters was quantified with a Phosphor Imager (Molecular Dynamics, CA USA), using data from three separate experiments.

The pFIS1 cDNA hybridised to a mRNA in Hoshangabad flax which increased in abundance after infection with the flax rust CH5 FIG. 3A). The increase in pFIS1 mRNA paralleled the development of infection with rust. In the early stage of infection (1 and 2 days post inoculation) the level of RNA is almost unchanged. Later (5–6 days after inoculation) when many mesophyll cells are infected with rust, the level of mRNA homologous to pFIS1 increased 10 fold, consistent with the expected pattern of induction for an SRR structural gene. The data shown in FIG. 2b indicate, however, that the number of leaf cells which contribute to this 10-fold overall increase in expression is small suggesting that the actual level of Fis1 gene induction per cell is much greater than 10-fold. Clearly, the 10-fold induction observed for the whole leaf is subject to a significant dilution effect from the contribution of the vast majority of cells in which no induction occurs.

The Fis1 mRNA is approximately 1.9 kb in size. To check that there was approximately equal loading of RNA, a low abundance cDNA (pFCS1 Flax Control Sequence) whose mRNA does not change was used to probe the same northern blot (FIG. 3B). Slightly less hybridization was detected in leaves 6 days after inoculation. This minor decrease may reflect a dilution effect due to the increase in the proportion of fungal RNA, thus causing a dilution of plant transcripts.

EXAMPLE 9

Expression of the SR Structural Gene Fis1 is not Induced in a Resistant Rust Interaction To determine whether expression of the SR structural gene Fis1 is induced during a resistant rust infection, northern hybridisations were performed on Forge flax infected with the flax rust CH5 as described in the preceding Examples, using the pFIS1 cDNA insert as a hybridisation probe.

In the resistant reaction, there was no increase in the observed levels of fis1 mRNA over a 5 day period (FIG. 4A). In contrast, a 5-fold increase (on average) was observed in the level of the control anionic peroxidase mRNA, at the very early stages of the resistant infection (FIG. 4B). The pattern of accumulation of Fis1 mRNA was unlike the induction pattern of a gene for a typical PR protein. These data and the data from Example 8 suggest that the SR structural gene, Fis1 is regulated by distinct cellular mechanisms to those processes which regulate host cell gene expression during a resistant interaction between said host and a rust fungus.

EXAMPLE 10

Isolation of the Maize Homologue of the Flax Fis1 Gene

In order to isolate maize cDNAs similar to the flax cDNA (pFIS1) degenerate oligonucleotide primers to two regions (the GPL and EEP motifs shown in Table 2) of the flax protein (FIS1) were designed. The nucleotide sequences of the digonucleotides used are set forth in SEQ ID Nos: 5, 6 and 7.

The fragments were then cloned into the Promega vector pGEM-T utilizing the "A overhang" added by Taq polymerse.

The expected size of the amplification product is approximately 700 bp, based on the Fis1 structural gene sequence. However, the PCR reactions produced at least three additional DNA fragments, 2 smaller and one larger than the expected 700 base pair fragment was used for further experiments because it was assumed to have GPL and EEP motifs in the same position as FIS1.

The template cDNA for PCR was synthesized from maize RNA, extracted from 3 week old maize plants 6 days after a susceptible infection with a maize rust. Total RNA was treated with Rnase free DNAse (DnaseQ) prior to cDNA synthesis, using the conditions supplied by, Promega. The reverse transcriptase reactions used 20 µg of total RNA and was primed with 200 µg of oligo d(T) in a 25 µl reactions using MMV reverse transcriptase from New England Biolabs in the recommended conditions. After the reverse transcription 0.5 µl of this reactions was used in a 2 µl PCR reactions. The PCR conditions were as follows, 10 mM Kcl, 10 mM Tris pH8.3, 1.5 mM MgCl, 2 µM each primers, 2 mM each dNTP and 1 unit of Taq polymerase from Boehringer Mannheim. The cycling parameters were: (94° C., 1 min; 45° C., 30 sec; 73° C., 2 min) 6×; (94° C., 10 sec; 45° C., 20 sec; 73+ C., 2 min) 32×; (94° C., 20 sec; 45° C., 20 sec; 73 ° C., 3.5 min) 1× using a Corbett Research thermal cycler. The primers were, EEP=5' AAA/g GAA/g ATA/t/c TTT/c GGI CCI TT 3' (SEQ ID NO: 5 ) and GPL=5' ATA/t/c ACI CCI TTT/c AAT/c TTT/c CC 3' (SEQ ID NO: 6) (I=inosine).

The products of the PCR reaction were separated on a TBE, 1% agarose gel and the 700 base pair fragment was eluted from the gel using the Qiagen gel extract kit.

The 700 base pair PCR product was then sequenced using an ABI automated sequencer. The sequence was used to search the data bases for similar sequences. The closest match to the maize sequence was that of the flax gene Fis1. This gave a blast score of 494, while the next highest score was 90 for a comparison to p5C dehydrogenase (1-pyrroline-5 -carboxylate dehydrogenase), an aldehyde dehydrogenase from *Bacillus subtilis*. The maize Mis1 structural gene is 72% identical over 633 nucleotides to the flax Fis1 structural gene at the nucleotide sequence level and 84% identical over 204 amino acids at the amino acid level. A comparison of the derived maize Mis1 and flax Fis1 polypeptides is provided in FIG. 5.

EXAMPLE 11

Expression of the Maize SR Structural Gene Mis1 in a Susceptible Interaction with *Puccinia sorghi* Race 1

Maize RNA was electrophoresed using standard denaturing formaldehyde gels (Maniatis et al., 1982 ) to separate 30 µg of total RNA. The RNA was then transferred with 20×SSC to Hybond N membranes (Amersham International, UK). DNA probes were labelled with [α-$^{32}$P]dCTP using the Megaprime system (Amersham). The amounts of $^{32}$P-labelled probe hybridizing to the filters was quantified with a Phosphor Imager (Molecular Dynamics, CA USA), using data from three separate experiments.

The maize Mis1 structural gene hybridised to a mRNA which increased in abundance after infection with the maize rust *Puccinia sorghi* race 1 (FIG. 6). The increase in Mis1 mRNA observed is consint with the expected pattern of induction for an SR structural gene.

EXAMPLE 12

Identification of Further Genes Related Fis1 and Mis1

To determine whether other cereal crop plant species contain SRR promoters and SR structural genes related to Fis1 or Mis1, genomic DNA was isolated from seedlings of barley, oats, wheat and maize and transferred to a membrane support and probed with the Mis1 SR structural gene sequence.

The data indicate the presence of SR-regulated genes such as Fis1 and Mis1 in all species examined (FIG. 7). Those skilled in the art will be aware that the demonstration of such sequences in other plants provides a means for their subsequent isolation.

EXAMPLE 13

Expression of the Barnase Gene Under Control of the Fis1 Promoter in Transgenic Plants The barnase structural gene is placed operably under control of the Fis1 promoter sequence by replacing the GUS gene present in the binary vector described above, in "Example 7" with the coding region of the barnase gene. Such methods are well within the means of those ordinarily skilled in the art, without undue experimentation.

The resultant genetic construct comprising the barnase coding region placed operably behind the Fis1 promoter is then introduced into Hoshangabad flax plants by Agrobacterium-mediated transformation procedures as described in Example 7. Transgenic plants are selected on kanamycin containing media and screened for expression of the barnase gene using conventional northern hybridisation, RNase protection or PCR approaches.

The regenerted transformed plants are subsequently infected with a flax rust capable of forming a susceptible interaction with the host plant, in particular the strain CH5, to determine whether the transgenic plants exhibit improved resistance to the flax rust. Control experiments ar performed using non-transformed isogenic flax plants of similar age and grown under identical conditions.

Statistically-significant protection (p<0.05) is afforded the transgenic plants by the expression of the barnase gene under control of the flax Fis1 gene promoter, following a susceptible interaction with *Melwnpsora lini*. In particular, although infection rates of non-transformed control plants and transformed plants are similar within the first 24 hr post-infection, the level of lesions in the transformed plants is markedly reduced within 14 days post-infection and the transformed plants recover their vigour rapidly. Thus, the approach of expressing a cytotoxin gene under the control of an SRR promoter sequence such as Fis1 is useful in providing protection against fungal pathogens in a susceptible interaction.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

REFERENCES

1. An et al (1985) EMBO J. 4:277–284.
2. Ausubel, F. M, Brent, R., Kingston, R. E., Moore, D. D., Seidman, J. G., Smith, J. A. and Struhl, K (1987) Current Protocols in Molecular Biology, Wiley Interscience (ISBN 047140338).
3. Collinge, D. B. and Slusarenko, A. J. (1987) Plant Mol. Biol. 9:389–410.
4. Crossway et al (1986) Mol. Gen. Genet. 202:179–185.
5. Dixon, R. E. and Lamb, C. J. (1990) Ann. Rev. Plant Physio. Plant Mol. Biol. 41:339–367.
6. Douillard and Hoffman (1981) Basic Facts about Hybridomas. In: Compendium of Immunology Vol II (ed. Schwarz).
7. Ellis, J. G., Finnegan, E. J. and Lawrence, G. J. (1992) Theor. and Applied Genetics 85:46–54.
8. Fromm et al. (1985) Proc. Natl. Acad. Sci. (USA) 82:5824–5828.
9. Haseloff, J. and Gerlach, W. L (1988) Nature 334:586–594.
10. Hempel, J., Nicholas, H. and Lindahl, R. (1993) Protein Sci. 2:1890–1900.
11. Henikoff, S. and Henikoff, J. G. (1991) Nucl. Acids Res. 19:6565–6572.
12. Herrera-Estrella et al. (1983 a) Nature 303:209–213.
13. Herrera-Estrella et al. (1983 b) EMBO J. 2:987–995.
14. Herrera-Estrella et al. (1985) In: Plant Genetic Engineering, Cambridge University Press, NY, pp 63–93.
15. Keen, N. T. (1992) Plant Mol. Biol. 19:109–122.
16. Kohler and Milstein (1975) Nature 256:495–499.
17. Kohler and Milstein (1976) Eur.J. Immunology 6:511–519.
18. Maniatis, T., Fritsch, E. F. and Sambrook, J. (1982). Molecular Cloning: A Laboratory Manual, Cold Spring Harbor, N.Y.:Cold Spring Harbor Laboratory.
19. Marineau, C., Matton, D. P. and Brisson, N. (1987) Plant Mol. Biol. 9:335–342.
20. Ohashi, Y. and Ohshima, M. (1992) Plant Cell Physiol. 33:819–826.
21. Pazkowski et al. (1984) EMBO J. 3:2717–2722
22. Sutton, B. C. S. and Shaw, M. (1986) Can. J. Bot. 64:13–18
23. van Loon, L. C. (1985) Plant Mol. Biol. 4:111–116.

What is claimed is:

1. An isolated promoter sequence which activates expression of a structural gene to which it is operably connected in a transformed plant in response to infection of said plant with a fungal pathogen in a susceptible interaction, wherein said promoter sequence comprises a nucleotide sequence of the plant-expresssible promoter contained in the gene construct deposited under AGAL Accession No. N96/027087.

2. A chimeric gene which comprises the promoter sequence of claim 1.

3. The chimeric gene according to claim 2 contained in the microorganism deposited under AGAL Accession No. N96/027087.

4. The chimeric gene according to claim 2, wherein the promoter sequence is operably linked to a structural gene.

5. The chimeric gene according to claim 4, wherein the structural gene is a reporter gene.

6. The chimeric gene according to claim 5, wherein said reporter gene is selected from the group consisting of GUS, chloramphenicol acetyltransferase and firefly luciferase.

7. The chimeric gene according to claim 4 wherein said structural gene is a SR structural gene.

8. A transgenic plant transformed with the chimeric gene according to claim 4.

9. A transgenic plant transformed with the chimeric gene according to claim 5.

10. A transgenic plant transformed with the chimeric gene according to claim 6.

11. A transgenic plant transformed with the chimeric gene according to claim 7.

12. A transgenic progeny plant of the plant according to claim 8.

13. A method of producing a plant with induced expression of a structural gene on infection with a fungal pathogen in a susceptible interaction, said method comprising the steps of transforming a plant cell with the chimeric gene of claim 4 and regenerating a whole plant from said plant cell.

14. The method according to claim 13, wherein the susceptible interaction is selected from the group consisting of:

(i) *Puccinia graminis* infection of wheat, barley or rye;
(ii) *Puccinia striformis* infection of wheat or rye;
(iii) *Puccinia recondita* infection of rye or wheat;
(iv) *Puccinia hordei* infection of barley;
(v) *Puccinia coronata* infection of oat;
(vi) *Puccinia sorghi* infection of maize;
(vii) *Puccinia polysora* infection of maize;
(viii) *Puccinia purpurea* infection of sorghum;
(ix) *Puccinia sacchari* infection of sugar cane;
(x) *Puccinia kuehnii* infection of sugar cane;
(xi) *Puccinia arachidis* infection of peanut;
(xi) *Puccinia stachmanii* infection of cotton;
(xii) *Uromyces striatus* medicaginis infection of alfalfa;
(xiii) *Uromyces phaseoli* infection of phaseolus beans;
(xiv) *Hemileia vastatnx* infection of coffee;
(xv) *Melampsora lini* infection of flax;
(xvi) *Gymnosporangium juniperi-virginianae* infection of cedar or apple;
(xvii) *Cronartium ribicola* infection of white pine; and
(xviii) *Cronartium fusiforme* infection of loblolly or slash pine.

15. The method according to claim 14, wherein the susceptible interaction is between *Melampsora lini* and flax or between Puccinia spp. and maize.

16. The method according to claim 15 wherein the susceptible interaction is between *Puccinia sorghi* and maize.

17. The method according to claim 15 wherein the susceptible interaction is between *Melampsora lini* and flax.

* * * * *

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 1853 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 54..1706

(xi) SEQUENCE DESCRIPTION: SEQ ID NO:1:

```
ATCAGAGGTC GCCATAGAGA TCATTTCCAC TCCAATCAAG CCCTCTGACC ATC ATG          56
                                                          Met
                                                          1

TAC AGG CCA CTT GTT GCC AGG TTG CTG CGA GAC AGC GTC GCT ACC CGA        104
Tyr Arg Pro Leu Val Ala Arg Leu Leu Arg Asp Ser Val Ala Thr Arg
            5                   10                  15

AAG GGC TCG TCC CAT TTC GCC CGG AGG TTT TCT CAT TCT TTG CCC TTC        152
Lys Gly Ser Ser His Phe Ala Arg Arg Phe Ser His Ser Leu Pro Phe
        20                  25                  30

GCG ACC GTA GAT GCG GAG GAG CTA TCT GGT GCT AAA CCA GCT GAA GTG        200
Ala Thr Val Asp Ala Glu Glu Leu Ser Gly Ala Lys Pro Ala Glu Val
    35                  40                  45

CTT AAC TTG GTT CAG GGG AAT TGG GGA GGT TCT TCC AGT TGG CAC ACG        248
Leu Asn Leu Val Gln Gly Asn Trp Gly Gly Ser Ser Ser Trp His Thr
50                  55                  60                  65

GTG GTT GAT CCT TTA AAC GGA GAA CCG TTT ATC AAA GTT GCT GAA GTA        296
Val Val Asp Pro Leu Asn Gly Glu Pro Phe Ile Lys Val Ala Glu Val
                70                  75                  80

GAC GAG ACA GAA ATC AAG CCA TTT GTG GAG AGC TTG TCC AAG TGC CCT        344
Asp Glu Thr Glu Ile Lys Pro Phe Val Glu Ser Leu Ser Lys Cys Pro
            85                  90                  95

AAA CAT GGA CTG CAC AAC CCC TTT AAG TCG CCT GAG AGG TAT CTT CTG        392
Lys His Gly Leu His Asn Pro Phe Lys Ser Pro Glu Arg Tyr Leu Leu
        100                 105                 110

TAT GGG GAC ATA TCT ACA AAG GCA GGA CAC ATG CTT TCC ATA CCA AAG        440
Tyr Gly Asp Ile Ser Thr Lys Ala Gly His Met Leu Ser Ile Pro Lys
    115                 120                 125

GTG TCG GAG TTC TTT GCA AGG CTA ATA CAA AGA GTT GCC CCG AAG AGT        488
Val Ser Glu Phe Phe Ala Arg Leu Ile Gln Arg Val Ala Pro Lys Ser
130                 135                 140                 145

TAC CAC CAG GCT CTT GGT GAA GTT CAA GTC ACC CAG AAG TTT TTT GAG        536
Tyr His Gln Ala Leu Gly Glu Val Gln Val Thr Gln Lys Phe Phe Glu
                150                 155                 160

AAC TTC ACT GGT GAT CAG GTT CGT TTC TTG GCA AGA TCA TTT GGA GTG        584
Asn Phe Thr Gly Asp Gln Val Arg Phe Leu Ala Arg Ser Phe Gly Val
            165                 170                 175

CCG GGA AAC CAT CTT GGT CAG CAA AGT AAT GGC TTC CGA TGG CCT TTT        632
Pro Gly Asn His Leu Gly Gln Gln Ser Asn Gly Phe Arg Trp Pro Phe
        180                 185                 190

GGT CCT GTT GCA ATA ATC ACT CCA TTC AAT TTC CCA CTA GAG ATT CCG        680
Gly Pro Val Ala Ile Ile Thr Pro Phe Asn Phe Pro Leu Glu Ile Pro
    195                 200                 205
```

```
GTT CTT CAG TTG ATG GGT GCT TTA TAC ATG GGC AAC AAA CCC CTT CTT       728
Val Leu Gln Leu Met Gly Ala Leu Tyr Met Gly Asn Lys Pro Leu Leu
210             215                 220                 225

AAA GTT GAT AGC AAG GTG TCC ATT GTT ATG GAA CAA ATG ATG AGA CTA       776
Lys Val Asp Ser Lys Val Ser Ile Val Met Glu Gln Met Met Arg Leu
                230                 235                 240

CTT CAC TAT TGC GGT TTG CCT GTG GGA GAT GCT GAC TTT GTC AAC TCG       824
Leu His Tyr Cys Gly Leu Pro Val Gly Asp Ala Asp Phe Val Asn Ser
            245                 250                 255

GAT GGG AAG GCT ATG AAC AAG ATA CTA CTG GAG GCT AAT CCC CGG ATG       872
Asp Gly Lys Ala Met Asn Lys Ile Leu Leu Glu Ala Asn Pro Arg Met
        260                 265                 270

ACA TTG TTT ACT GGT AGC TCA AGA GTT GCG GAG AAG TTG GCT CTT GAC       920
Thr Leu Phe Thr Gly Ser Ser Arg Val Ala Glu Lys Leu Ala Leu Asp
    275                 280                 285

TTA AAG GGC CGC ATC AAG TTG GAA GAT GCA GGA TTT GAC TGG AAA ATT       968
Leu Lys Gly Arg Ile Lys Leu Glu Asp Ala Gly Phe Asp Trp Lys Ile
290                 295                 300                 305

CTA GGG CCT GAT GTC AAT GAG GCA GAC TAT GTT GCT TGG GTG TGT GAC      1016
Leu Gly Pro Asp Val Asn Glu Ala Asp Tyr Val Ala Trp Val Cys Asp
                310                 315                 320

CAA GAT GCA TAT GCA TGT AGT GGT CAG AAG TGC TCT GCA CAA TCC ATT      1064
Gln Asp Ala Tyr Ala Cys Ser Gly Gln Lys Cys Ser Ala Gln Ser Ile
            325                 330                 335

CTA TTC ATG CAC GAG AAC TGG GCT GCT ACT CCA CTC ATT TCG AGA TTG      1112
Leu Phe Met His Glu Asn Trp Ala Ala Thr Pro Leu Ile Ser Arg Leu
        340                 345                 350

AAG GAG CTT GCA GAG AGG AGA AAG TTG GAA GAT CTA ACT GTT GGC CCT      1160
Lys Glu Leu Ala Glu Arg Arg Lys Leu Glu Asp Leu Thr Val Gly Pro
    355                 360                 365

GTC CTC ACT GTT ACC ACC GAA GCG ATG CTG GAT CAC CTG AAC AAG TTG      1208
Val Leu Thr Val Thr Thr Glu Ala Met Leu Asp His Leu Asn Lys Leu
370                 375                 380                 385

CTT CAG ATA CCG GGA GCT AAG CTG CTC TTT GGC GGC AAG CCT CTG GAG      1256
Leu Gln Ile Pro Gly Ala Lys Leu Leu Phe Gly Gly Lys Pro Leu Glu
                390                 395                 400

AAT CAT ACC ATT CCA TCC ATA TAT GGT GCC GTG AAA CCA ACA GCC GTG      1304
Asn His Thr Ile Pro Ser Ile Tyr Gly Ala Val Lys Pro Thr Ala Val
            405                 410                 415

TAT GTC CCT CTG GAA GAA ATT CTG AAA GTG AGT AAC TAT GAA CTT GTT      1352
Tyr Val Pro Leu Glu Glu Ile Leu Lys Val Ser Asn Tyr Glu Leu Val
        420                 425                 430

ACA AAG GAA ATC TTC GGA CCA TTC CAG GTT GTA ACG GAG TAC AAG AAC      1400
Thr Lys Glu Ile Phe Gly Pro Phe Gln Val Val Thr Glu Tyr Lys Asn
    435                 440                 445

AGT CAA CTT CCT ATG GTT CTG GAA GCT TTG GAG AGG ATG CAC GCA CAT      1448
Ser Gln Leu Pro Met Val Leu Glu Ala Leu Glu Arg Met His Ala His
450                 455                 460                 465

TTA ACA GCT GCT GTA GTT TCG AAC GAT CAG CTG TTT TTG CAG GAA GTC      1496
Leu Thr Ala Ala Val Val Ser Asn Asp Gln Leu Phe Leu Gln Glu Val
                470                 475                 480

ATC GGG AAC ACT GTG AAT GGC ACA ACT TAT GCC GGG TTG CGA GCA AGA      1544
Ile Gly Asn Thr Val Asn Gly Thr Thr Tyr Ala Gly Leu Arg Ala Arg
            485                 490                 495

ACG ACA GGA GCT CCG CAG AAT CAT TGG TTT GGA CCA GCT GGA GAC CCG      1592
Thr Thr Gly Ala Pro Gln Asn His Trp Phe Gly Pro Ala Gly Asp Pro
        500                 505                 510

AGA GGT GCA GGG ATT GGA ACA CCA GAA GCC ATT AAA CTT GTC TGG TCT      1640
Arg Gly Ala Gly Ile Gly Thr Pro Glu Ala Ile Lys Leu Val Trp Ser
```

```
                515                   520                   525
TGC CAC CGA GAG ATC ATT TAC GAT ATC GGC CCT GTA TCA CAC CAT TGG         1688
Cys His Arg Glu Ile Ile Tyr Asp Ile Gly Pro Val Ser His His Trp
530                     535                   540                   545

GAA ATT CCT CCA TCC ACT TAGAGAGAGA GTGAGAGATT TGTAAAACTG                1736
Glu Ile Pro Pro Ser Thr
                550

TTGAGATGTA GCTGACTGAT CCATGTATCA GAAGTAGGCA TTCATCAGCC CGTGTACCG        1796

TACTTTCTAC GAATAAAAAT GCCGGGAAGT CTGTAGATCA AAAAAAAAAA AAAAAAA          1853
```

(2) INFORMATION FOR SEQ ID NO:2:

(i) SEQUENCE CHARACTERISTICS:
        (A) LENGTH: 551 amino acids
        (B) TYPE: amino acid
        (D) TOPOLOGY: linear (ii) MOLECULE TYPE: protein (xi) SEQUENCE DESCRIPTION: SEQ ID NO:2:

```
Met Tyr Arg Pro Leu Val Ala Arg Leu Leu Arg Asp Ser Val Ala Thr
  1               5                  10                  15

Arg Lys Gly Ser Ser His Phe Ala Arg Arg Phe Ser His Ser Leu Pro
                 20                  25                  30

Phe Ala Thr Val Asp Ala Glu Glu Leu Ser Gly Ala Lys Pro Ala Glu
             35                  40                  45

Val Leu Asn Leu Val Gln Gly Asn Trp Gly Gly Ser Ser Trp His
         50                  55                  60

Thr Val Val Asp Pro Leu Asn Gly Glu Pro Phe Ile Lys Val Ala Glu
 65                  70                  75                  80

Val Asp Glu Thr Glu Ile Lys Pro Phe Val Glu Ser Leu Ser Lys Cys
                 85                  90                  95

Pro Lys His Gly Leu His Asn Pro Phe Lys Ser Pro Glu Arg Tyr Leu
                100                 105                 110

Leu Tyr Gly Asp Ile Ser Thr Lys Ala Gly His Met Leu Ser Ile Pro
            115                 120                 125

Lys Val Ser Glu Phe Phe Ala Arg Leu Ile Gln Arg Val Ala Pro Lys
130                 135                 140

Ser Tyr His Gln Ala Leu Gly Glu Val Gln Val Thr Gln Lys Phe Phe
145                 150                 155                 160

Glu Asn Phe Thr Gly Asp Gln Val Arg Phe Leu Ala Arg Ser Phe Gly
                165                 170                 175

Val Pro Gly Asn His Leu Gly Gln Gln Ser Asn Gly Phe Arg Trp Pro
            180                 185                 190

Phe Gly Pro Val Ala Ile Ile Thr Pro Phe Asn Phe Pro Leu Glu Ile
        195                 200                 205

Pro Val Leu Gln Leu Met Gly Ala Leu Tyr Met Gly Asn Lys Pro Leu
    210                 215                 220

Leu Lys Val Asp Ser Lys Val Ser Ile Val Met Glu Gln Met Met Arg
225                 230                 235                 240

Leu Leu His Tyr Cys Gly Leu Pro Val Gly Asp Ala Asp Phe Val Asn
                245                 250                 255

Ser Asp Gly Lys Ala Met Asn Lys Ile Leu Leu Glu Ala Asn Pro Arg
            260                 265                 270

Met Thr Leu Phe Thr Gly Ser Ser Arg Val Ala Glu Lys Leu Ala Leu
        275                 280                 285
```

```
Asp Leu Lys Gly Arg Ile Lys Leu Glu Asp Ala Gly Phe Asp Trp Lys
    290                 295                 300

Ile Leu Gly Pro Asp Val Asn Glu Ala Asp Tyr Val Ala Trp Val Cys
305                 310                 315                 320

Asp Gln Asp Ala Tyr Ala Cys Ser Gly Gln Lys Cys Ser Ala Gln Ser
                325                 330                 335

Ile Leu Phe Met His Glu Asn Trp Ala Ala Thr Pro Leu Ile Ser Arg
            340                 345                 350

Leu Lys Glu Leu Ala Glu Arg Arg Lys Leu Glu Asp Leu Thr Val Gly
        355                 360                 365

Pro Val Leu Thr Val Thr Thr Glu Ala Met Leu Asp His Leu Asn Lys
    370                 375                 380

Leu Leu Gln Ile Pro Gly Ala Lys Leu Leu Phe Gly Gly Lys Pro Leu
385                 390                 395                 400

Glu Asn His Thr Ile Pro Ser Ile Tyr Gly Ala Val Lys Pro Thr Ala
                405                 410                 415

Val Tyr Val Pro Leu Glu Glu Ile Leu Lys Val Ser Asn Tyr Glu Leu
            420                 425                 430

Val Thr Lys Glu Ile Phe Gly Pro Phe Gln Val Val Thr Glu Tyr Lys
        435                 440                 445

Asn Ser Gln Leu Pro Met Val Leu Glu Ala Leu Glu Arg Met His Ala
    450                 455                 460

His Leu Thr Ala Ala Val Val Ser Asn Asp Gln Leu Phe Leu Gln Glu
465                 470                 475                 480

Val Ile Gly Asn Thr Val Asn Gly Thr Thr Tyr Ala Gly Leu Arg Ala
                485                 490                 495

Arg Thr Thr Gly Ala Pro Gln Asn His Trp Phe Gly Pro Ala Gly Asp
            500                 505                 510

Pro Arg Gly Ala Gly Ile Gly Thr Pro Glu Ala Ile Lys Leu Val Trp
        515                 520                 525

Ser Cys His Arg Glu Ile Ile Tyr Asp Ile Gly Pro Val Ser His His
    530                 535                 540

Trp Glu Ile Pro Pro Ser Thr
545                 550

(2) INFORMATION FOR SEQ ID NO:3:

(i) SEQUENCE CHARACTERISTICS:
        (A) LENGTH: 347 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

ATAAACCTCC TATGACTTAC CGAGCAAATG CGGCTGCGGA ACCACTCGAA TCTACCACTC      60

TTGCATCAAA ACCACCGCCG TAGCTGCCGA CGTTAAAGTA TCCAGAGATA GCAAGTGACG     120

AGGCAGTGAA GTTAGTAGAG GAAACAGAAA CTGCAGTAAA ATCATTTCAA ATAACAGAGA    180

GAGAAGAGTT AGCGGCAAAG AGAAGGAGAC TACCATGGAA ACAAAGCTTG AAAACGAAGG    240

AAAGAGGAAT CGCAAAAGAA GAGAGCGATC TTAAAGCTGC ATTTGGCCTC CCTTTCGCGG    300

TGTGTTCACT CTCCCTCTAT CTCTACTTGC GTCTTGTGTT CTCGGCA                  347

(2) INFORMATION FOR SEQ ID NO:4:
```

```
    (i) SEQUENCE CHARACTERISTICS:
        (A) LENGTH: 161 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

ATAAACCTCC ATCACTACCT CTAAAGCTGC ACGGCTGACA CCGCAACACC AAATAACTTG      60

CCACATTTTC TCTCTATCCA AATCCAAAAT CGACGTCTCT TTCTCCTCCT CATCACTGAG     120

TTTGTTCATA CTTGCCCAAC CAAAAGCTTG GTACTTTTAG C                        161

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Ns' at positions 3, 9, 12, 15, 18, and 21
            are purine,
            pyrimidine/adenine, pyrimidine,inosine,
            inosine, and pyrimidine, respectively (xi) SEQUENCE DESCRIPTION: SEQ ID NO:5:

AANGARATNT TNGGNCCNTT N                                               21

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Ns' at positions 3, 6, 9, 12, 15, 18, and 21 are
            pyrimidine/adenine, inosine, inosine,
            pyrimidine, pyrimidine, pyrimidine, and inosine,
            respectively (xi) SEQUENCE DESCRIPTION: SEQ ID NO:6:

ATNACNCCNT TNAANTTNCC N                                               21

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Ns' at positions 3, 6, 9, 12, 15, 18, 21,
            and 24 are pyrimidine, inosine, inosine, purine,
            purine, pyrimidine, inosine, and inosine, respectively (xi) SEQUENCE DESCRIPTION: SEQ ID NO:7:

TGNWSNGGNC ANAANTGNWS NGCN                                            24
```

(2) INFORMATION FOR SEQ ID NO:8:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:8:

```
Trp Pro Phe Gly Pro Val Ala Ile Ile Thr Pro Phe Asn Phe Pro Leu
 1               5                  10                  15

Glu Ile Pro Val Leu Gln Leu Met Gly Ala Leu Tyr Met Gly Asn Lys
            20                  25                  30

Pro Leu Leu Lys Val
        35
```

(2) INFORMATION FOR SEQ ID NO:9:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:9:

```
Arg Met Thr Leu Phe Thr Gly Ser Ser Arg Val Ala Glu Lys Leu Ala
 1               5                  10                  15

Leu Asp Leu Lys Gly Arg Ile Lys Leu Glu Asp
            20                  25
```

(2) INFORMATION FOR SEQ ID NO:10:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:10:

```
Asp Ala Tyr Ala Cys Ser Gly Gln Lys Cys Ser Ala Gln Ser Ile Leu
 1               5                  10                  15

Phe Met His Glu
        20
```

(2) INFORMATION FOR SEQ ID NO:11:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:11:

```
Asn Tyr Glu Leu Val Thr Lys Glu Ile Phe Gly Pro Phe Gln Val Val
 1               5                  10                  15

Thr Glu Tyr Lys Asn Ser Gln Leu Pro Met Val Leu Glu Ala
            20                  25                  30
```